United States Patent
Rydbeck et al.

[11] Patent Number: 5,958,376
[45] Date of Patent: Sep. 28, 1999

[54] IODINATED X-RAY CONTRAST MEDIA

[75] Inventors: Anna Rydbeck, Staffanstorp; Torsten Almen, Falsterbo; Mikkel Thaning, Tygelsjövägen; Sven Göran Andersson, Lomma; Lars-Göran Wistrand, Lund, all of Sweden; Klaes Golman, Rungsted Kyst, Denmark

[73] Assignee: Nycomed Imaging AS, Oslo, Norway

[21] Appl. No.: 08/793,927

[22] PCT Filed: Sep. 22, 1995

[86] PCT No.: PCT/GB95/02264

§ 371 Date: Jun. 27, 1997

§ 102(e) Date: Jun. 27, 1997

[87] PCT Pub. No.: WO96/09285

PCT Pub. Date: Mar. 28, 1996

[30] Foreign Application Priority Data

Sep. 23, 1994 [GB] United Kingdom ............... 9419206

[51] Int. Cl.$^6$ ............... A61K 49/04; C07C 273/00; C07C 233/00
[52] U.S. Cl. ............... 424/9.451; 424/9.452; 564/55; 564/176; 564/179
[58] Field of Search ............... 424/9.451, 9.453, 424/9.452; 564/153, 139, 330, 55, 158, 161, 244, 176, 179; 514/726

[56] References Cited

U.S. PATENT DOCUMENTS

| 2,708,678 | 5/1955 | Papa . | |
|---|---|---|---|
| 2,776,241 | 1/1957 | Priewe et al. | 424/9.45 |
| 3,409,662 | 11/1968 | Larsen et al. . | |
| 3,794,729 | 2/1974 | Wohl et al. . | |
| 5,618,977 | 4/1997 | Dugast-Zrihen et al. . | |

FOREIGN PATENT DOCUMENTS

| A 0049860 | 4/1992 | European Pat. Off. . |
| 0 0501875 | 9/1992 | European Pat. Off. . |
| A-1 603 923 | 11/1993 | European Pat. Off. . |
| 2 737 802 | 3/1979 | Germany . |
| WO-A-88/09328 | 12/1988 | WIPO . |
| WO-A-90/11094 | 10/1990 | WIPO . |
| WO A 9109007 | 6/1991 | WIPO . |
| WO-A-91/13636 | 9/1991 | WIPO . |
| WO-A-94/14478 | 7/1994 | WIPO . |

OTHER PUBLICATIONS

Almén, Torsten; *Development of Nonionic Contrast Media*, Investigative Radiology vol. 20, Jan.–Feb. Supplement 1985.

Anal. Chem. (Ancham. 00032700); 82; vol. 54 (3); pp. 481–485, Northeastern Univ. College. Pharm. Allied Health Profess.; Boston, MA 02115, Corkill et al., Mar. 1982.

J. Chomatogr. (Jocram); 70; vol. 50 (3); pp. 507–510, Med. Found. of Buffalo, N.Y., 1970, Volpert et al.

Chemical Abstracts, vol. 082, No. 3, Jan. 20, 1975; Hoffenberg et al.

Mass Spectrom. Biochem. Med. Symp. (29CWAZ); 74, pp. 303–312, Clin. Res. Cont.; Div Clin. Invest; Chemical Abstracts 9$^{th}$ Collective Index; p. 4441CS, 1975.

*Primary Examiner*—José G. Dees
*Assistant Examiner*—Michael G. Hartley
*Attorney, Agent, or Firm*—Bacon & Thomas

[57] ABSTRACT

The invention provides iodinated bis phenyl compounds, useful as X-ray contrast agents, of formula (I) (wherein each $C_6R_5$ moiety may be the same or different; each denotes a hydrogen or iodine atom or a group M, two or three non-adjacent R groups on each $C_6R_5$ moiety denoting iodine atoms and one, two or three R groups on each $C_6R_5$ moiety denoting M groups; X denotes a group providing a 1, 2 or 3 atom chain linking the two $C_6R_5$ groups, preferably where X is or contains in the bridging chain a carbonyloxy group each $C_6R_5$ group being a triodophenyl group or a group in which each R is other than hydrogen; and each M is independently a non-ionic hydrophilic moiety, M preferably being a non-ionic hydrophilic moiety comprising a monohydroxy- or polyhydroxy-alkyl group) and isomers, especially stereoisomers and rotamers, thereof.

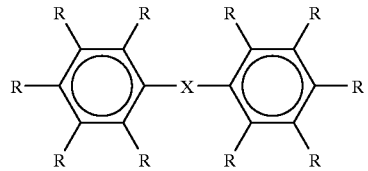

(I)

11 Claims, No Drawings

IODINATED X-RAY CONTRAST MEDIA

This invention relates to improvements in and relating to contrast media, and in particular iodinated X-ray contrast media.

Contrast media may be administered in medical imaging procedures, for example X-ray, magnetic resonance and ultrasound imaging, to enhance the image contrast in images of a subject, generally a human or non-human animal body. The resulting enhanced contrast enables different organs, tissue types or body compartments to be more clearly observed or identified. In X-ray imaging, the contrast media function by modifying the X-ray absorption characteristics of the body sites into which they distribute.

Clearly however the utility of a material as a contrast medium is governed largely by its toxicity, by its diagnostic efficacy, by other adverse effects it may have on the subject to which it is administered, and by its ease of storage and ease of administration.

Since such media are conventionally used for diagnostic purposes rather than to achieve a direct therapeutic effect, when developing new contrast media there is a general desire to develop media having as little as possible an effect on the various biological mechanisms of the cells or the body as this will generally lead to lower animal toxicity and lower adverse clinical effects.

The toxicity and adverse biological effects of a contrast medium are contributed to by the components of the medium, e.g. the solvent or carrier as well as the contrast agent and its components (e.g. ions where it is ionic) and metabolites.

The following major contributing factors to contrast media toxicity and adverse effects have been identified:

the chemotoxicity of the contrast agent, the osmolality of the contrast medium, and the ionic composition (or lack thereof) of the contrast medium.

In coronary angiography, for example, injection into the circulatory system of contrast media has been associated with several serious effects on cardiac function. These effects are sufficiently severe as to place limitations on the use in angiography of certain contrast media.

In this procedure, for a short period of time a bolus of contrast medium rather than blood flows through the circulatory system and differences in the chemical and physico-chemical nature of the contrast medium and the blood that it temporarily replaces can give rise to undesirable effects, e.g. arrhythmias, QT-prolongation, and, especially, reduction in cardiac contractile force and occurrence of ventricular fibrillation. There have been many investigations into these negative effects on cardiac function of infusion of contrast media into the circulatory system, e.g. during angiography, and means for reducing or eliminating these effects have been widely sought.

Early injectable ionic X-ray contrast agents, based on triiodophenylcarboxylate salts, were particularly associated with osmotoxic effects deriving from the hypertonicity of the contrast media injected.

This hypertonicity causes osmotic effects such as the draining out of water from red-blood cells, endothelial cells, and heart and blood vessel muscle cells. Loss of water makes red blood cells stiff and hypertonicity, chemotoxicity and non-optimal ionic make-up separately or together reduce the contractile force of the muscle cells and cause dilation of small blood vessels and a resultant decrease in blood pressure.

The osmotoxicity problem was addressed by the development of the non-ionic triiodophenyl monomers, such as iohexol, which allowed the same contrast effective iodine concentrations to be attained with greatly reduced attendant osmotoxicity effects.

The drive towards reduced osmotoxicity led in due course to the development of the non-ionic bis(triiodophenyl) dimers, such as iodixanol, which reduce osmotoxicity associated problems still further allowing contrast effective iodine concentrations to be achieved with hypotonic solutions.

Examples of bis triodophenyl dimers linked via aminocarbonylalkylene carbonyl amino chains are given in WO 91/09007 of Mallinckrodt.

The ability to achieve contrast effective iodine concentrations without taking solution osmolality up to isotonic levels (about 300 mOsm/kg $H_2O$) further enabled the contribution to toxicity of ionic imbalance to be addressed by the inclusion of various plasma cations, as discussed for example in WO-90/11094 and WO-91/13636 of Nycomed Imaging AS.

However X-ray contrast media, at commercial high iodine concentrations of about 300 mgI/ml, have relatively high viscosities, ranging from about 15 to about 60 mPas at ambient temperature with the dimeric media generally being more viscous than the monomeric media. Such viscosities pose problems to the administrator of the contrast medium, requiring relatively large bore needles or high applied pressure, and are particularly pronounced in paediatric radiography and in radiographic techniques which require rapid, bolus administration, e.g. in angiography.

This viscosity problem is recognised to pose a serious barrier towards the development of high opacity x-ray contrast agents, especially in the case of high iodine value compounds, and its solution offers the opportunity either to produce contrast agent solutions with higher than conventional iodine concentrations or solutions with conventional iodine concentrations but with lower viscosities, which can more easily be injected and which are usable in a greater range of diagnostic investigations.

The present invention addresses the viscosity problem encountered with the prior art materials and thus viewed from one aspect the invention provides iodinated bis phenyl compounds, useful as X-ray contrast agents, of formula I

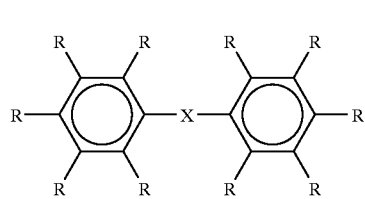

(I)

(wherein each $C_6R_5$ moeity may be the same or different; each R denotes a hydrogen or iodine atom or a group M, two or three non-adjacent R groups on each $C_6R_5$ moiety denoting iodine atoms and one, two or three R groups on each $C_6R_5$ moiety denoting M groups, each $C_6R_5$ moiety being a triiodophenyl group or a group in which each R is other than hydrogen; X denotes a group providing a 1, 2 or 3 atom chain linking the two $C_6R_5$ groups; and each M is independently a non-ionic hydrophilic moiety, M preferably being a non-ionic hydrophilic moiety comprising a monohydroxy- or polyhydroxy-alkyl group) and isomers, especially stereoisomers and rotamers, thereof.

It is found that the short chain dimer compounds according to the invention possess desirably low viscosities in aqueous solution.

The compounds of formula I are preferably asymmetric. This can be achieved by the use of an asymmetric 2 or 3 atom chain-forming group X and/or by selection of non-identical $C_6R_5$ groups, i.e. by non-identical substitution of the iodophenyl end groups. Asymmetric molecules are preferred as they have been found to have better water-solubility.

Such non-identical substitution of the phenyl end groups, the $C_6R_5$ moieties, may be achieved by having different numbers or positions of iodine substitution and/or by different numbers, positions or identities of M substitution. To maximize iodine loading, triodophenyl end groups, i.e. groups of formula

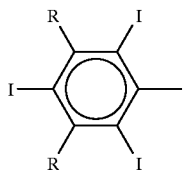

are preferred, and in these the two R groups may be the same or different, although preferably both represent M groups.

Where a phenyl end group is disubstituted by iodine, it is preferably of formula

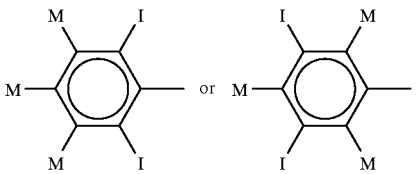

(where M again may be the same or different).

Generally, diiodophenyl-diiodophenyl dimers will be less preferred than the diiodophenyl-triiodophenyl or triiodophenyl-triiodophenyl dimers, due primarily to their reduced iodine loading, i.e. 4 rather than 5 or 6 iodines per diner molecule. Indeed the triiodophenyl-triiodophenyl diners are generally preferred due to their higher iodine loading.

The solubilizing groups M may be any of the non-ionizing groups conventionally used to enhance water solubility. Suitable groups include for example straight chain or branched $C_{1-10}$-alkyl groups, preferably $C_{1-5}$ groups, optionally with one or more $CH_2$ or CH moieties replaced by oxygen or nitrogen atoms and optionally substituted by one or more groups selected from oxo, hydroxy, amino, carboxyl derivative, and oxo substituted sulphur and phosphorus atoms. Particular examples include polyhydroxyalkyl, hydroxyalkoxyalkyl and hydroxypolyalkoxyalkyl and such groups attached to the phenyl group via an amide linkage such as hydroxyalkylaminocarbonyl, N-alkyl-hydroxyalkylaminocarbonyl and bis-hydroxyalkylaminocarbonyl groups. Preferred among such groups are those containing 1, 2, 3, 4, 5 or 6, especially 1, 2 or hydroxy groups, e.g.
—$CONH$—$CH_2CH_2OH$
—$CONH$—$CH_2CHOHCH_2OH$
—$CONH$—$CH(CH_2OH)_2$
—$CON(CH_2CH_2OH)_2$
as well as other groups such as
—$CONH_2$
—$CONHCH_3$
—$QCOCH_3$
—$N(COCH_3)H$
—$N(COCH_3)C_{1-3}$-alkyl
—$N(COCH_3)$-mono, bis or tris-hydroxy $C_{1-4}$-alkyl
—$N(COCH_2OH)$-mono, bis or tris-hydroxy $C_{1-4}$-alkyl
—$C(COCH_3)$ (mono, bis or tris-hydroxy $C_{1-4}$-alkyl)$_2$
—$N$—$(COCH_2OH)_2$
—$CON$ $(CH_2CHOHCH_2OH)$ $(CH_2CH_2OH)$
—$CONH$—$C(CH_2OH)_3$ and
—$CONH$—$CH(CH_2OH)$ $(CHOHCH_2OH)$.

In general, the M groups will preferably each comprise a polyhydroxy $C_{1-4}$-alkyl group, such as 1,3-dihydroxyprop-2-yl or 2,3-dihydroxyprop-1-yl.

Other such M groups as are conventional within the field of triiodophenyl X-ray contrast agents may also be used and the introduction of M groups onto iodophenyl structures may be achieved by conventional techniques.

In the compounds of the invention, the linker group X is conveniently a 1, 2 or 3 membered chain comprising carbon, nitrogen, oxygen or sulphur atoms, e.g.
a O, S, N or C one atom chain,
a NN, NC, NS, CC or CO two atom chain, or a NCN, OCN, CNC, OCO, NSN, CSN, COC, OCC or CCC three atom chain,
for example:
an oxygen atom or a group $NR^1$, CO, $SO_2$ or $CR_2^1$;
a group COCO, $CONR^1$, $COCR_2^1$, $SOCR_2^1$, $SO_2NR^1$, $CR_2^1CR_2^1$, $CR_2^1NR^1$ or $CR^1_2O$;
a group $NR^1CONR^1$, $OCONR^1$, $CONR^1CO$, $CONR^1CR^1_2$, OCOO, $CR^1_2OCR^1_2$, $OCR^1_2CO$, $CR^1_2CONR^1$, $CR^1_2CR^1_2CR^1_2$, $COCR^1R^1CO$, $CR^1_2NR^1CR^1_2$, $CR^1_2SO_2NR^1$, $CR^1_2OCO$, or $NR^1SO_2NR^1$;
where $R^1$ is hydrogen or a $C_{1-6}$-alkyl or alkoxy group optionally substituted by hydroxy, alkoxy, oxa or oxo (e.g. a polyhydroxyalkyl, formyl, acetyl, hydroxyl, alkoxy or hydroxyalkoxy group), or where attached to a carbon $R^1$ may also be a hydroxyl group.

Advantageously, the X group is not symmetrical. This may be achieved for example by asymmetrical substitution of a symmetrical chain (e.g. N—C—N substituted as $NHCONR^1$) or by selection of an asymmetric chain (e.g. OCN substituted as $OCONR^1$). In particular, it is preferred that the linker group X should be polar and also that it should be hydrophilic.

Thus examples of preferred structures according to the invention include:

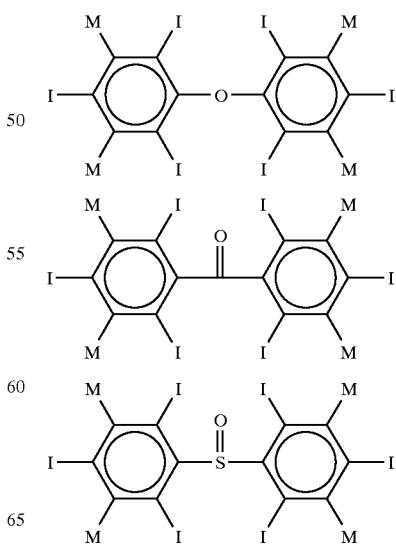

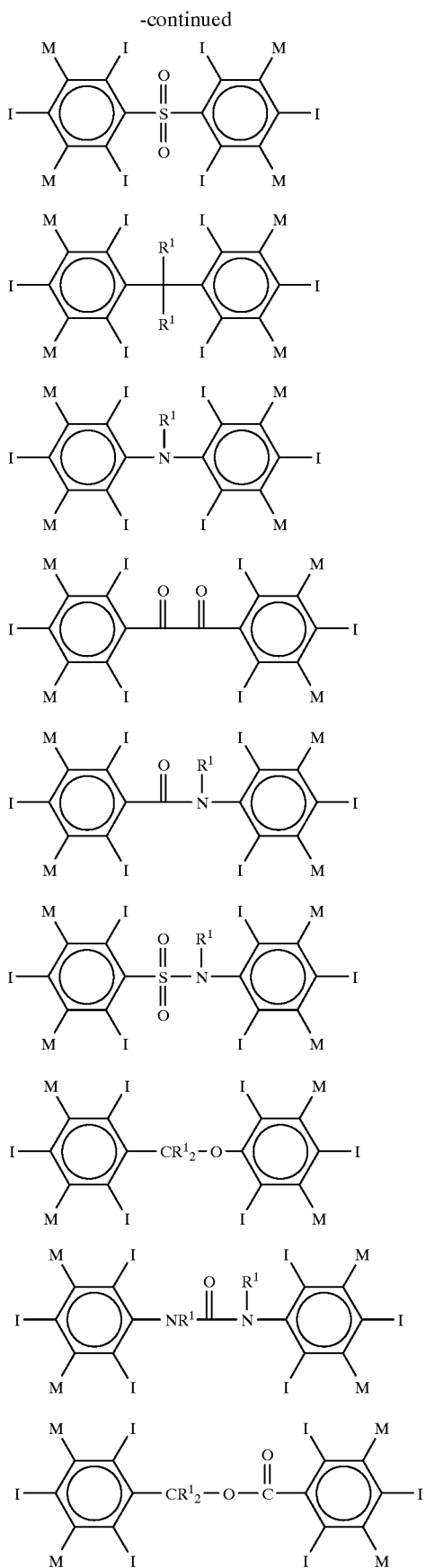
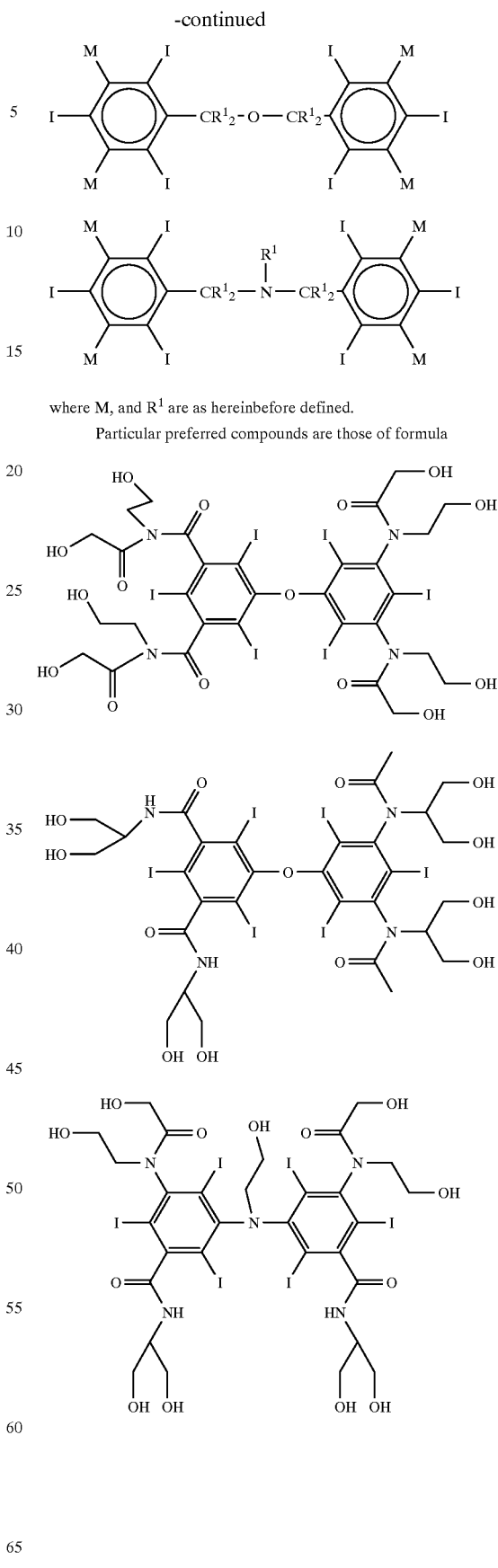
where M, and R¹ are as hereinbefore defined.
Particular preferred compounds are those of formula

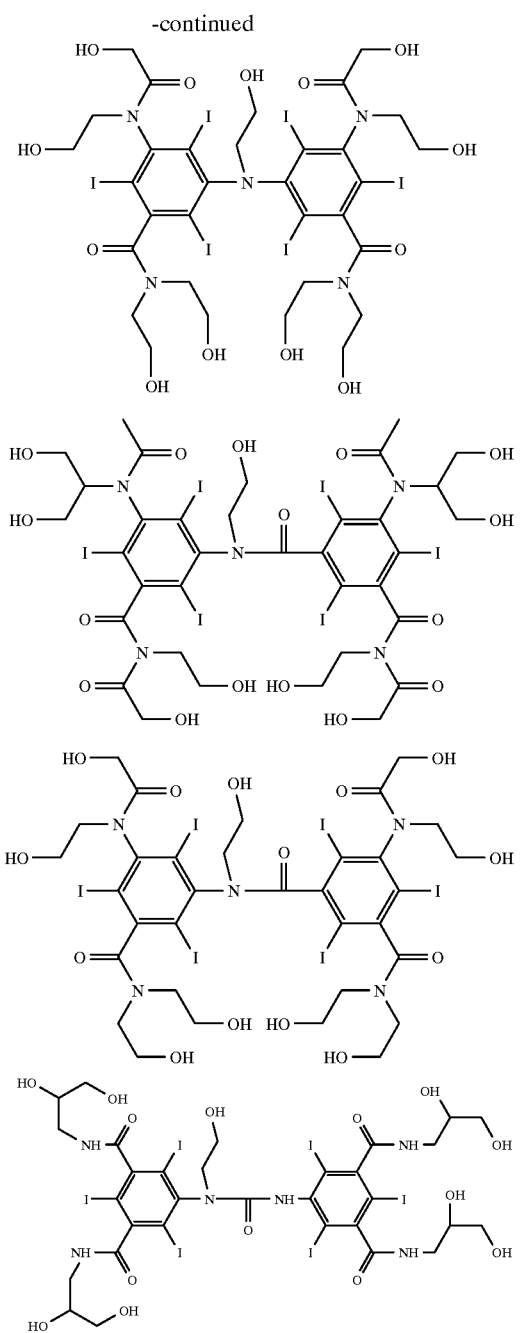

The compounds of the invention may in general be prepared in three stages: (a) dimer formation, (b) iodination of phenyl groups and (c) substitution of phenyl groups and/or optionally linker moieties by solubilizing moieties.

While, in theory, stages (a), (b) and (c) can be performed in any order, it will generally be preferred to perform the dimer formation step before the iodination step and, for reasons of economy, it will be preferred to perform the iodination step at as late a stage in the synthesis as is feasible so as to reduce iodine wastage. The dimer formation stage may itself be a multi-step procedure with an appropriate activated linker first being attached to one monomer before the resulting linker-monomer conjugate is reacted with a second monomer. Alternatively, dimer formation may be by way of reaction of similarly or cooperatively substituted monomers with the conjugation of the monomers leading to dimer formation.

Where desired the linker group X may be produced by modification, e.g. substitution, oxidation or reduction, of a precursor linker, e.g. in a precursor monomer.

In all cases conventional synthetic methods well known in the literature (eg methods analogous to those used and described for the production of the dimers referred to in WO-94/14478) may be used.

The dimeric compounds of the invention may be used as X-ray contrast agents and to this end they may be formulated with conventional carriers and excipients to produce diagnostic contrast media.

Thus viewed from a further aspect the invention provides a diagnostic composition comprising a compound of formula I (as defined above) together with at least one physiologically tolerable carrier or excipient, e.g. in aqueous solution in water for injections optionally together with added plasma ions or dissolved oxygen.

The contrast agent compositions of the invention may be at ready-to-use concentrations or may be formulated in concentrate form for dilution prior to administration. Generally compositions in ready-to-use form will have iodine concentrations of at least 100 mgI/ml, preferably at least 150 mgI/ml, with concentrations of at least 300 mgI/ml, e.g. 320 to 400 mgI/ml being generally preferred. The higher the iodine concentration the higher the diagnostic value but equally the higher the solution's viscosity and osmolality. Normally the maximum iodine concentration for a given compound will be determined by its solubility, and by the upper tolerable limits for viscosity and osmolality.

For contrast media which are administered by injection, the desirable upper limit for solution viscosity at ambient temperature (20° C.) is 30 mPas; however viscosities of up to 50 or even up to 60 mPas can be tolerated although their use in paediatric radiography will then generally be contraindicated. For contrast media which are to be given by bolus injection, e.g. in angiographic procedures, osmotoxic effects must be considered and preferably osmolality should be below 1 Osm/kg $H_2O$, especially below 850 mOsm/kg $H_2O$, in particular within 50 or less, preferably within 10, mOsm of isotonicity (about 300 mOsm/kg $H_2O$).

With the dimers of the invention, such viscosity, osmolality and iodine concentration targets can readily be met. Indeed effective iodine concentrations may be reached with hypotonic solutions. It may thus be desirable to make up solution tonicity by the addition of plasma cations so as to reduce the toxicity contribution which derives from ionic imbalance effects following bolus injection. Such cations will desirably be included in the ranges suggested in WO-90/01194 and WO-91/13636.

Preferred plasma cation contents for the contrast media of the invention, especially contrast media for angiography, are as follows:

sodium 2 to 100, especially 15 to 75, particularly 20 to 70, more particularly 25 to 35 mM calcium up to 3.0, preferably 0.05 to 1.6, especially 0.1 to 1.2, particularly 0.15 to 0.7 mM potassium up to 2, preferably 0.2 to 1.5, especially 0.3 to 1.2, particularly 0.4 to 0.9 mM magnesium up to 0.8, preferably 0.05 to 0.6, especially 0.1 to 0.5, particularly 0.1 to 0.25 mM The plasma cations may be presented, in whole or in part, as counterions in ionic contrast agents. Otherwise they will generally be provided in the form of salts with physiologically tolerable counteranions, e.g. chloride, sulphate, phosphate, hydrogen carbonate, etc., with plasma anions especially preferably being used.

Besides plasma cations, the contrast media may contain other counterions where the dimer is ionic and such counterions will of course preferably be physiologically tolerable. Examples of such ions include alkali and alkaline earth metal ions, ammonium, meglumine, ethanolamine, diethanolamine, chloride, phosphate, and hydrogen carbonate. Other counterions conventional in pharmaceutical formulation may also be used. The compositions moreover may contain further components conventional in X-ray contrast media, e.g. buffers, etc.

The invention will now be described further with reference to the following non-limiting Examples.

EXAMPLE 1

N,N'-bis[2,4,6-triiodo-3,5-bis(2,3-dihydroxypropylaminocarbonyl)phenyl]-urea a. 5-Amino-2,4,6-triiodo-N,N'-bis(2,3-diacetoxypropyl)-isophthalamide 5-Amino-2,4,6-triiodo-N,N'-bis(2,3-dihydroxypropyl)-isophthalamide (14.08 g, 0.02 mol), which had been prepared according to GB-A-1548594 was suspended in pyridine (200 ml) and acetic anhydride (57.1 g, 0.56 mol) was added dropwise with stirring and cooling. After stirring overnight, the mixture was poured into ethyl acetate (300 ml) and 20% aqueous HCl (200 ml). After extraction, the organic phase was washed with 2 M aqueous HCl (20 ml), brine (70 ml), dried ($Na_2SO_4$) and evaporated. Yield 17.4 g (100%). The crude material was used without further purification, since analysis by HPLC and $^1H$ NMR indicated, that the product was >97% pure.

$^1H$ NMR (acetone-$d_6$): 8.76–8.83 (m, 2H, NH), 5.50 (br s, 2H, $NH_2$), 5.20–5.32 (m, 2H), 4.43 (dd, $J_1$=11.8 Hz, $J_2$=3.4 Hz, 2H), 4.29 (dd, $J_1$=11.8 Hz, $J_2$=6.0 Hz), 3.69–3.86 (m, 2H), 3.49–3.63 (m, 2H), 1.95–2.07 (m, 12H). MS (ESP): 706 (M+1).

b. N,N'-bis[2,4,6-triiodo-3,5-bis(2,3-diacetoxypropylaminocarbonyl)phenyl]-urea

5-Amino-2,4,6-triiodo-N,N'-bis(2,3-diacetoxypropyl)-isophthalamide (10.4 g, 0.012 mol) was dissolved in dry dioxane (20 ml) and a 20% solution of phosgene in toluene (3.1 ml) was added. The mixture was stirred for 1 week in a closed, thick-walled container at ambient temperature. After evaporation, the residue was purified by preparative HPLC. Yield 10.0 g (94%).

$^1H$ NMR: 8.24–8.98 (m, 6H, NH), 5.07 (br s, 4H), 4.12–4.35 (m, 8H), 3.31–3.60 (m, 8H), 2.00 (s, 24H, $CH_3CO$). MS (ESP): 1771 ($M^+$).

c. N,N'-bis[2,4,6-triiodo-3,5-bis(2,3-dihydroxypropylaminocarbonyl) phenyl]-urea N,N'-bis[2,4,6-triiodo-3,5-bis(2,3-diacetoxypropylaminocarbonyl)phenyl]-urea (4.0 g, 2.26 mmol) was dissolved in a 1:1 mixture of water and methanol (25 ml) containing NaOH (1.44 g, 36 mmol). After stirring for 6 h at 40° C., the solution was treated with a strongly acidic ion exchange resin (Amberlyst 15), the solvent was separated and evaporated to give pure product. Yield: 3.24 g (100%).

$^1H$ NMR (DMSO-$d_6$): 7.98–8.60 (m, 6H, NH), 4.65–4.80 (m, 4H), 4.44–4.57 (m, 4H), 3.62–3.75 (m, 4H), 3.02–3.55 (m, 16H). $^{13}C$ NMR (DMSO-$d_6$): 170.7, 170.4, 170.3, 151.8, 151.7, 150.1, 143.5, 100.9, 100.8, 100.7, 100.5, 100.3, 89.8, 89.6, 70.1, 70.0, 64.1, 42.7, 42.6. MS (ESP): 1458 ($M^+$+$Na^+$).

EXAMPLE 2

N,N'-bis[2,4,6-triiodo-3,5-bis(2,3-dihydroxypropylaminocarbonyl)phenyl]-N-methyl-urea N,N'-bis[2,4,6-triiodo-3,5-bis(2,3-dihydroxypropylaminocarbonyl)phenyl]-urea (7.32 g, 5.1 mmol) was dissolved in 2 M aqueous NaOH (10 ml) and methyl iodide (0.95 ml) was added. The mixture was stirred at ambient temperature for 60 h, treated with a strongly acidic ion exchange resin (Amberlyst 15) evaporated and purified by preparative HPLC. Yield 4.7 g (63%) of the product as a white solid.

$^1H$ NMR (DMSO-$d_6$): 8.80 (br d, 1H, NH), 8.42 (br d, 3H, NH), 8.05 (br d, 1H, NH), 4.42–4.85 (m, 8H), 3.01–3.78 (m, 23H). $^{13}C$ NMR (DMSO-$d_6$): 170.2, 170.1, 170.0, 152.6, 152.5, 150.7, 150.3, 150.2, 149.5, 144.2, 101.3, 101.2, 100.0, 99.5, 90.5, 90.1, 70.5, 70.3, 64.4, 64.3, 43.1, 42.9, 36.0. MS (ESP): 1470 ($M^+$+$Na^+$).

EXAMPLE 3

N,N'-bis[2,4,6-triiodo-3,5-bis(2,3-dihydroxypropylaminocarbonyl)phenyl]-N-hydroxyethyl-urea N,N'-bis[2,4,6-triiodo-3,5-bis(2,3-dihydroxypropylaminocarbonyl)phenyl]-urea (2.0 g, 1.4 mmol) was dissolved in water (13 ml) containing 2 M NaOH (7 ml). 2-Bromoethanol (1 g, 8.4 mmol) was added and the mixture was stirred at ambient temperature for 60 h, treated with a strongly acidic ion exchange resin (Amberlyst 15) evaporated and purified by preparative HPLC. Yield: 1.45 g (70%) of the product as a white solid.

$^1H$ NMR (DMSO-$d_6$):9.10–9.38 (m, 1H, NH), 7.90–8.65 (m, 4H, NH), 3.02–3.91 (m, 24H). $^{13}C$ NMR (DMSO-$d_6$): 170.2, 153.2, 150.9, 150.3, 149.1, 144.1, 101.3, 100.9, 100.7, 100.3, 90.6, 89.8, 70.5, 70.4, 70.1, 64.4, 63.2, 60.6, 53.2, 43.1, MS (ESP): 1502 ($M^+$+$Na^+$).

EXAMPLE 4

N,N'-bis[2,4,6-triiodo-3-(2-hydroxyethylaminocarbonyl)-5-(1,3-dihydroxyprop-2-ylaminocarbonyl)-phenyl]-urea a. 1-Amino-2,4,6-triiodo-3,5-isophthalic acid dichloride.

1-Amino-2,4,6-triiodo-3,5-isophthalic acid (200 g, 0.358 mol) was added to thionyl chloride (150 ml). The mixture was stirred at reflux temperature for 6 h and then allowed to cool to ambient temperature. After evaporation, the solid residue was dissolved in ethyl acetate (300 ml) which was again evaporated to dryness. The residue was dissolved in ethyl acetate (2000 ml) and the resulting solution was washed with a solution of NaCl (250 g) and $NaHCO_3$ (120 g) in water (2000 ml) which had been cooled to 0° C. The organic phase was separated, washed with brine and dried ($Na_2SO_4$). Evaporation gave 202 g (94%) of the product as a white solid.

$^1H$ NMR (DMSO-$d_6$): 10.79 (br s, 2H). $^{13}C$ NMR (DMSO-$d_6$): 170.1, 149.7, 149.4, 78.94, 78.90. MS(ESP, m/e): 595, 593 ($M^+$).

b. 1-Amino-2,4,6-triiodo-3-(2-acetoxyethylaminocarbonyl)-5-(1,3-diacetoxyprop-2-ylaminocarbonyl)benzene.

1-Amino-2,4,6-triiodo-3,5-isophthalic acid dichloride (10.0 g, 16.8 mmol) was dissolved in dry N,N-dimethylacetamide (DMAC, 80 ml) and triethylamine (14 ml) was added. After addition of 2-amino-1,3-propanediole (2.14 g, 23.55 mmol), the mixture was stirred for 60 h. Ethanolamine (5.0 ml) was added and the mixture was stirred for another 24 h. After evaporation of the solvents, the solid residue was dissolved in pyridine (250 ml) and acetic anhydride (200 ml) was added. After stirring for 20 h, the solvents were evaporated and the residue was dissolved in ethyl acetate. The solution was washed with water, diluted aqueous HCl, aqueous $NaHCO_3$, dried ($MgSO_4$) and evaporated. Chromatography on silica using ethyl acetate/heptane (6:1) followed by preparative HPLC (RP-18, acetonitrile-:water 35:65) gave 4.74 g (35%) of the product.

$^1$H NMR (CDCl$_3$): 6.01–6.17 (2 br s, 2H, NH), 5.11 (br s, 2H, NH$_2$), 4.59–4.67 (m, 1H, CH), 4.22–4.40 (m, 6H, CH$_2$O), 3.69–3.78 (m, 2H, NCH$_2$), 2.12 (s, 3H), 2.08 (s, 6H). MS(ESP, m/e): 823 ([M+Na]$^+$), 801 ([M+1]$^+$).

c. N,N'-bis[2,4,6-triiodo-3-(2-hydroxyethylaminocarbonyl)-5-(1,3-dihydroxyprop-2-ylaminocarbonyl)-phenyl]urea.

1-Amino-2,4,6-triiodo-3-(2-acetoxyethylaminocarbonyl)-5-(1,3-diacetoxyprop-2-ylaminocarbonyl)benzene (0.967 g, 1.20 mmol) was mixed with phosgene (8.86 ml of a 20% solution in toluene) and dioxane (3 ml) in a thick-walled, stoppered flask which was then kept at 60° C. for 18 h. The mixture was allowed to cool to ambient temperature and the solvents were evaporated. Dioxane (5 ml) was added and distilled off at atmospheric pressure. This procedure was repeated twice. Dioxane (10 ml), 1-amino-2,4,6-triiodo-3-(2-acetoxyethylaminocarbonyl)-5-(1,3-diacetoxyprop-2-ylaminocarbonyl)benzene (0.926 g, 1.16 mmol) and mercury trifluoroacetate (26 mg, 0.23 mmol) were added and the solvent was again distilled off at atmospheric pressure during 1 h. Dioxane (10 ml) was added and the mixture was stirred at ambient temperature for 16 h. The solvent was distilled off once more, and, after evaporation, the residue was dissolved in a mixture of methanol (35 ml) and 0.4M aqueous NaOH (50 ml). After stirring for 2 h, the solution was neutralized using a strongly acidic cation exchange resin, filtered and lyophilized. The residue was purified by preparative HPLC. Yield: 0.43 g (27%).

$^1$H NMR (DMSO-d$_6$): 8.03–8.59 (m, 6H), 4.42–4.77 (m, 6H), 3.10–3.83 (m, 18H).

EXAMPLE 5

N,N'-bis[2,4,6-triiodo-3-(2-hydroxyethylaminocarbonyl)-5-(1,3-dihydroxyprop-2-ylaminocarbonyl)-phenyl]-N-hydroxyethylurea N,N'-bis[2,4,6-triiodo-3-(2-hydroxyethylaminocarbonyl)-5-(1,3-dihydroxyprop-2-ylaminocarbonyl)-phenyl]urea (0.27 g, 0.2 mmol) from Example 4 was dissolved in water (7 ml) containing 2M aqueous NaOH (1.0 ml) and 2-bromoethanol (0.084 ml, 1.2 mmol). After stirring for 20 h, the solution was neutralized with a strongly acidic cation exchange resin and evaporated to dryness. The residue was purified by preparative HPLC. Yield 138 mg (50%).

$^1$H NMR (DMSO-d$_6$): 9.06–9.22 (m, 1H), 8.03–8.46 (m, 4H), 4.22–4.69 (m, 7H), 3.43–3.87 (m, 22H).

EXAMPLE 6

N,N'-bis[2,4,6-triiodo-3-(2-hydroxyethylaminocarbonyl)-5-(1,3-dihydroxyprop-2-ylaminocarbonyl)-phenyl]-N-(2,3-dihydroxypropyl)urea N,N'-bis[2,4,6-triiodo-3-(2-hydroxyethylaminocarbonyl)-5-(1,3-dihydroxyprop-2-ylaminocarbonyl)-phenyl]urea (0.25 g, 0.18 mmol) was dissolved in water (5 ml) followed by 2M aqueous NaOH (2.1 ml) and, after 5 min, bromopropane-2,3-diol (0.196 ml) was added. The solution was stirred for 4 days, neutralized with a strongly acidic cation exchange resin and evaporated to dryness. Purification by preparative HPLC gave 38 mg (14%) of the product as a white solid. MS (ESP, m/e): 1450 (M$^+$).

EXAMPLE 7

N,N'-bis[2,4,6-triiodo-3-(2-hydroxyethylaminocarbonyl)-5-(2,3-dihydroxypropylaminocarbonyl)-phenyl]urea a. 1-Amino-2,4,6-triiodo-3-(2-acetoxyethylaminocarbonyl)-5-(2,3-diacetoxypropylaminocarbonyl)benzene.

1-Amino-2,4,6-triiodo-3,5-isophthalic acid dichloride (3.03 g, 5.1 mmol), prepared according to Example 4a, was added to a solution of triethylamine (4.26 ml) in DMAC (20 ml). A solution of 1-amino-2,3-propanediol (0.51 g, 5.6 mmol) in DMAC (3 ml) was added and, after stirring for 16 h at ambient temperature, ethanolamine (1.55 g, 25.5 mmol) was added. After stirring for another 16 h, the solvents were evaporated, the residue was dissolved in pyridine (75 ml), acetic anhydride (60 ml) was added and the solution was stirred for 17 h. The solvents were evaporated, the residue was dissolved in ethyl acetate and the solution was washed with water, 0.2M aqueous HCl solution, aqueous NaHCO$_3$, dried (MgSO$_4$) and evaporated. Purification by preparative HPLC gave 1.28 g (31%) of the product as a white solid.

$^1$H NMR (DMSO-d$_6$): 8.60–8.71 (m, 2H), 5.42–5.51 (m, 1H), 5.02–5.13 (m, 1H), 4.24–4.33 (m, 1H), 4.08–4.21 (m, 3H), 3.32–3.49 (m, 5H), 2.00 (2s, 9H). MS (ESP, m/e): 823 ([M+Na]$^+$), 801 (M+1)

b. N,N'-bis[2,4,6-triiodo-3-(2-hydroxyethylaminocarbonyl)-5-(2,3-dihydroxypropylaminocarbonyl)-phenyl]urea.

1-Amino-2,4,6-triiodo-3-(2-acetoxyethylaminocarbonyl)-5-(2,3-diacetoxypropylaminocarbonyl)benzene (1.99 g, 2.48 mmol) was dissolved in dioxane (7 ml) together with a solution of phosgene in toluene (20%, 18 ml) in a thick-walled flask. The mixture was heated to 60° C. for 16 h, and, after cooling to ambient temperature, the solvents were evaporated. Dioxane (10 ml) was added and distilled off at atmospheric pressure. This procedure was repeated 3 times. The residue was dissolved in dioxane (10 ml) containing mercury trifluoroacetate (35 mg) and 1-amino-2,4,6-triiodo-3-(2-acetoxyethylaminocarbonyl)-5-(2,3-diacetoxypropylaminocarbonyl)benzene (2.0 g, 2.50 mmol). The flask was heated and the solvent was distilled off slowly. Another portion of dioxane (10 ml) was added and then distilled off again. The residue was dissolved in a mixture of methanol (60 ml) and 0.22 M aqueous NaOH (90 ml) and, after stirring for 6 h, the solution was neutralized with a strongly acidic cation exchange resin. After evaporation of the solvents, the residue was purified by preparative HPLC to give 1.26 g (37%) of the product as a white solid.

$^1$H NMR (DMSO-d$_6$): 8.02–8.67 (m, 6H), 4.60–4.84 (m, 4H), 4.43–4.57 (m, 2H), 3.02–3.75 (m, 18H). $^{13}$C NMR (DMSO-d$_6$): 169.7, 169.5, 151.4, 150.0, 142.9, 99.9, 89.6, 70.1, 70.0, 69.9, 64.0, 59.2, 42.6, 41.7.

EXAMPLE 8

N,N'-bis[2,4,6-triiodo-3-(2-hydroxyethylaminocarbonyl)-5-(2,3-dihydroxypropylaminocarbonyl)phenyl]-N-hydroxyethylurea N,N'-Bis[2,4,6-triiodo-3-(2-hydroxyethylaminocarbonyl)-5-(2,3-dihydroxypropylaminocarbonyl)-phenyl]urea (0.216 g, 0.157 mmol) was dissolved in a mixture of water (6 ml) and 2 M aqueous NaOH (0.9 ml) together with 2-bromoethanol (0.067 ml). The mixture was stirred for 20 h, neutralized with a strongly acidic cation exchange resin and evaporated to dryness. Purification using preparative HPLC gave 105 mg (47%) of the product as a white solid.

¹H NMR (DMSO-d₆): 9.11–9.22 (m, 1H), 7.84–8.61 (m, 4H), 4.41–4.80 (m, 7H), 3.02–3.87 (m, 22H). ¹³C NMR (DMSO-d₆): 170.2, 169.9, 153.2, 151.0, 150.9, 150.4, 144.2, 144.1, 100.2, 70.5, 64.4, 60.6, 59.6, 43.1, 42.1. MS (ESP, m/e): 1420 (M⁺).

EXAMPLE 9

N,N'-bis[2,4,6-triiodo-3-(2-hydroxyethylaminocarbonyl)-5-(2,3-dihydroxypropylaminocarbonyl)phenyl]-N-(2,3-dihydroxypropyl)urea N,N'-Bis[2,4,6-triiodo-3-(2-hydroxyethylaminocarbonyl)-5-(2,3-dihydroxypropylaminocarbonyl)-phenyl]urea (0.353 g, 0.257 mmol) was dissolved in a mixture of water (8 ml) and 2M aqueous NaOH (0.9 ml) together with 1-bromo-2,3-dihydroxypropane (0.136 ml, 1.55 mmol). After stirring at room temperature for 160 h, the solution was neutralized using a strongly acidic cation exchange resin. After evaporation, the residue was purified using preparative HPLC. Yield: 100 mg (27%) of the product as a white solid.

¹H NMR (DMSO-d₆): 9.45–9.63 (m, 1H), 7.94–8.68 (m, 4H), 5.82–6.07 (m, 1H), 5.12 (br s, 1H), 4.43–4.80 (m, 6H), 4.13 (m, 1H), 3.04–3.97 (m, 14H). ¹³C NMR (DMSO-d₆): 169.8, 169.5, 153.5, 150.8, 150.5, 150.0, 149.9, 143.7, 99.8, 90.3, 70.0, 64.0, 59.2, 42.7, 41.7.

EXAMPLE 10

N,N'-bis[2,4,6-triiodo-3-acetamido-5-(2,3-dihydroxypropylaminocarbonyl)phenyl]urea a. N,N'-bis(3-nitro-5-carboxyphenyl)urea.

1-Nitro-3-aminobenzoic acid (9.11 g, 50 mmol) was mixed with phosgene (13 ml of a 20% solution in toluene) and Na₂CO₃ (7.4 g, 70 mmol) in toluene (20 ml). The mixture was stirred at 60° C. for 2 h and then at ambient temperature for 16 h. After addition of additional toluene (4 ml), stirring was continued at 100° C. for 9h. Toluene (4 ml) was added, and stirring was continued for 20 h at 40° C. After cooling to ambient temperature, the solution was poured into 1M aqueous HCl (200 ml). The off-white precipitate was filtered off, washed with a mixture of ethanol and 2M aqueous HCl (4 ml), filtered and dried. Yield: 8.2 g (84%).

¹H NMR (DMSO-d₆): 9.63 (s, NH, 2H), 8.65 (dd, $J_1=J_2=$ 22 Hz, 2H), 8.34 (dd, $J_1=1.6$ Hz, $J_2=1.5$ Hz, 2H), 8.18 (dd, $J_1=1.5$ Hz, $J_2=1.3$ Hz, 2H), 3.3–3.8 (br s, 2H, OH). ¹³C NMR (DMSO-d₆): 165.8, 152.7, 148.5, 141.4, 133.1, 125.3, 117.3, 116.6. MS (ESP, m/e): 389 (M⁺, 100%), 411 ([M+Na]⁺, 55%)

b. N,N'-bis(3-nitro-5-methoxycarbonylphenyl)urea.

N,N'-bis(3-nitro-5-carboxyphenyl)urea (0.5 g, 1.3 mmol) was dissolved in methanol (15 ml) containing concentrated sulfuric acid (0.5 ml) and the solution was stirred at 60° C. for 20 h. After cooling to ambient temperature, the solution was poured into water (40 ml). The yellowish precipitate was filtered off, washed with a saturated aqueous solution of NaHCO₃, water and dried. Yield 0.53 g (98%).

¹H NMR (DMSO-d₆): 9.78 (br s, NH, 1H), 8.68 (dd, $J_1=2.1$ Hz, $J_2=2.0$ Hz, 2H), 8.46 (dd, $J_1=2.2$ Hz, $J_2=2.0$ Hz, 2H), 8.23 (dd, $J_1=2.2$ Hz, $J_2=2.0$ Hz, 2H), 3.92 (s, OCH₃, 6H). ¹³C NMR (DMSO-d₆): 164.9, 153.1, 148.5, 142.0, 131.6, 124.9, 117.0, 116.9.

c. N,N'-bis[3-nitro-5-(2,3-dihydroxypropylaminocarbonyl)phenyl]urea.

N,N'-bis(3-nitro-5-methoxycarbonylphenyl)urea (0.209 g, 0.5 mmol) was heated with 1-amino-2,3-propanediol (0.114 g, 1.2 mmol) to 95° C. After 30 min, the pressure was reduced to 200 mm Hg and heating was continued for 3 h. The crude reaction mixture was purified by preparative HPLC giving 164 mg (61%) of the product as a white solid.

¹H NMR (DMSO-d₆): 9.61 (s, 2H), 8.79 (t, J=6.4 Hz, 2H), 8.67 (dd, $J_1=2.1$, $J_2=2.0$ Hz, 2H), 8.36 (dd, $J_1=2.1$ Hz, $J_2=2.0$ Hz, 2H), 8.25 (dd, $J_1=J_2=2.0$ Hz, 2H), 4.84 (d, J=4.5 Hz, OH, 2H), 4.58 (t, J=5.6 Hz, OH, 2H), 3.65 (m, 2H), 3.30–3.50 (m, 6H), 3.21 (m, 2H). ¹³C NMR (DMSO-d₆): 164.8, 152.6, 148.5, 141.1, 136.8, 124.2, 115.9, 115.4. MS (ESP, m/e): 537 (M⁺, 100%), 519 ([M-H₂O]⁺, 56%).

d. N,N'-bis[3-amino-5-(2,3-dihydroxypropylaminocarbonyl)phenyl]urea.

N,N'-bis[3-nitro-5-(2,3-dihydroxypropylaminocarbonyl) phenyl]urea (0.103 g, 0.19 mmol) was dissolved in a mixture of methanol (14 ml) and water (6 ml) containing 2 M aqueous HCl (0.2 ml) and a Pd/C catalyst (10%, 0.1 g). Hydrogenation was carried out at 60 psi. The catalyst was filtered off and the solvents were evaporated. The residue was redissolved in water and lyophilized giving 0.102 g (97%) of the product.

¹H NMR (D₂O): 7.60 (s, 4H), 7.29 (s, 2H), 3.74–3.82 (m, 2H), 3.38–3.54 (m, 4H), 3.22–3.37 (m, 4H). ¹³C NMR (D₂O): 168.6, 154.0, 139.9, 136.1, 131.1, 118.6, 118.5, 117.0, 116.9, 116.2, 70.1, 63.2, 42.4. MS (ESP, m/e): 477 (M⁺, 100%).

e. N,N'-bis[3-amino-2,4,6-triiodo-5-(2,3-dihydroxypropylaminocarbonyl)phenyl]urea.

N,N'-bis[3-amino-5-(2,3-dihydroxypropylaminocarbonyl)phenyl]urea (0.50 g, 0.91 mmol) was dissolved in a mixture of methanol (4 ml) and water (46 ml) and an aqueous solution of KICl₂ (6 mmol) was added. After adjustment of pH to 2 with aqueous HCl, the solution was stirred for 20 h at 40° C. After addition of an aqueous solution of NaHSO₃, the solvents were evaporated and the residue was triturated three times with a methanol-water (3:7) mixture giving 1.02 g (89%) of the product.

¹H NMR (DMSO-d₆): 8.41 (br s, 1H), 8.20–8.33 (m, 2H), 8.11–8.17 (d, J=7.0 Hz, 1H), 5.40 (br s, NH₂, 4H), 3.62–3.74 (m, 2H), 3.44–3.52 (m, 2H), 3.34–3.43 (m, 2H), 3.21–3.32 (m, 2H), 3.07–3.21 (m, 2H). ¹³C NMR (DMSO-d₆): 170.7, 170.6, 151.9, 149.3, 148.9, 143.1, 143.0, 142.8, 70.6, 70.4, 64.4, 43.1, 43.0. MS (ESP, m/e): 1232 (M⁺, 20%), 1254 ([M+Na]⁺, 100%), 1270 ([M+K]⁺, 50%).

f. N,N'-bis[3-acetamido-2,4,6-triiodo-5-(2,3-dihydroxypropylaminocarbonyl)phenyl]urea.

N,N'-bis[3-amino-2,4,6-triiodo-5-(2,3-dihydroxypropylaminocarbonyl)phenyl]urea (0.155 g, 0.126 mmol) was mixed with acetic anhydride (2 ml) and concentrated sulfuric acid (3 drops) was added. The mixture was stirred at 70° C. for 5 h and then at ambient temperature for 17 h. After evaporation of the solvent, the residue was dissolved in a mixture of methanol (2.5 ml) and water (0.4 ml), pH was adjusted to 10 with 10M aqueous NaOH and stirred at 50° C. for 5 h. After evaporation of the solvent, the residue was triturated with water and the solid was filtered off and dried. Yield 0.15 g (90%).

¹H NMR (DMSO-d₆): 9.80–10.10 (2 br s, 2H), 8.20–8.75 (m, 4H), 4.70 (s, OH, 2H), 4.48 (s, OH, 2H), 3.64–3.98 (m, 2H), 3.41–3.56 (m, 4H), 3.03–3.26 (m, 4H), 2.04 (s, 6H). ¹³C NMR (DMSO-d₆): 170.3, 170.2, 168.3, 168.2, 168.1, 151.9, 151.7, 150.3, 144.4, 144.3, 108.2, 108.1, 99.5, 99.4, 99.3, 99.2, 98.1, 98.0, 97.9, 70.6, 70.4, 64.4, 43.1, 23.5. MS (ESP, m/e): 1339 ([M+Na]⁺, 100%).

EXAMPLE 11

N,N'-bis[2,4,6-triiodo-3-(2-hydroxyacetamido)-5-(2,3-dihydroxypropylaminocarbonyl)-phenyl]urea a. N,N'-bis[3-amino-2,4,6-triiodo-5-(2,3-diacetoxypropylaminocarbonyl)phenyl]urea.

N,N'-bis[3-amino-2,4,6-triiodo-5-(2,3-dihydroxypropylaminocarbonyl)phenyl]urea (1.23 g, 1.0 mmol) was dissolved in a mixture of acetic anhydride (5 ml), pyridine (5.5 ml) and DMF (5 ml). The solution was stirred at room temperature for 65 h, and the solvents were evaporated. The residue was dissolved in $CH_2Cl_2$ (250 ml) and the solution was washed with water (2×50 ml) 0.1M aqueous HCl (50 ml), water (100 ml) and a saturated aqueous solution of $NaHCO_3$. After drying ($Na_2SO_4$) and evaporation, NMR and HPLC analysis of the residue showed an essentially pure product. Yield: 1.0 g (71%).

$^1$H NMR (DMSO-$d_6$): 8.73 (br s, 1H), 8.44–8.63 (m, 2H), 8.32–8.45 (m, 1H), 5.30–5.45 (s, $NH_2$, 4H), 5.02–5.16 (m, 2H), 4.10–4.37 (m, 4H), 1.80–2.05 (m, 12H). $^{13}$C NMR (DMSO-$d_6$): 170.8, 170.6, 170.3, 149.1, 148.9, 148.3, 147.8, 143.3, 143.2, 136.6, 124.4, 92.6, 92.0, 70.1, 70.0, 63.5, 21.5, 21.0. MS (ESP, m/e): 1400 ($M^+$, 100%).

b. N,N'-bis[2,4,6-triiodo-3-(2-acetoxyacetamido)-5-(2,3-diacetoxypropylaminocarbonyl)phenyl]urea.

N,N'-bis[3-amino-2,4,6-triiodo-5-(2,3-diacetoxypropylaminocarbonyl)phenyl]urea (1.0 g, 0.71 mmol) was dissolved in acetoxyacetyl chloride (5 ml) and the solution was stirred at ambient temperature for 24 h. After heating to 60° C. for 2.5 h, the solution was evaporated to dryness and the residue was triturated with water (40 ml). The tan-colored precipitate was filtered off, washed again with water (20 ml) and dried. Yield: 0.92 g (81%).

$^1$H NMR (DMSO-$d_6$): 10.05–10.30 (m, 2H), 8.62–9.06 (m, 2H), 8.22–8.58 (m, 2H), 5.02–5.15 (m, 2H), 4.66 (br s, 4H), 4.23–4.39 (m, 2H), 4.12–4.23 (m, 2H), 3.25–3.62 (m, 4H), 2.11 (s, 6H), 2.00 (s, 12H). $^{13}$C NMR (DMSO-$d_6$): 170.7, 170.4, 170.1, 165.7, 150.1, 150.0, 144.5, 144.4, 143.3, 143.2, 108.5, 108.3, 108.1, 97.6, 97.3, 70.0, 63.5, 62.6, 61.0, 21.5, 21.0. MS (ESP, m/e): 1599 ($M^+$, 100%), 1621 ([M+Na]$^+$, 23%).

c. N,N'-bis[2,4,6-triiodo-3-(2-hydroxyacetamido)-5-(2,3-dihydroxypropylaminocarbonyl)phenyl]urea.

N,N'-bis[2,4,6-triiodo-3-(2-acetoxyacetamido)-5-(2,3-diacetoxypropylaminocarbonyl)phenyl]urea (0.88 g, 0.55 mmol) was dissolved in a mixture of methanol (10 ml) and 2M aqueous NaOH (2.5 ml). After stirring for 15 min at ambient temperature, pH was adjusted to 4 with a strongly acidic ion exchange resin, and, after filtration, evaporated to dryness. The residue was purified by preparative HPLC. Yield: 0.58 g (78%).

$^1$H NMR (DMSO-$d_6$): 9.68–9.93 (m, 2H), 8.42–8.64 (m, 2H), 8.24–8.48 (m, 2H), 4.00 (s, OH, 6H), 3.60–3.73 (m, 6H), 3.36–3.54 (m, 6H), 3.04–3.38 (m, 4H). $^{13}$C NMR (DMSO-$d_6$): 171.0, 170.8, 170.6, 170.3, 170.2, 151.8, 151.7, 150.3, 150.2, 144.3, 144.1, 143.9, 143.8, 108.1, 108.0, 107.9, 99.5, 99.3, 97.9, 97.8, 97.7, 70.4, 64.4, 62.3, 43.1. MS (ESP, m/e): 1349 ($M^+$, 36%), 1379 ([M+Na]$^+$, 100%).

EXAMPLE 12

N,N'-bis[2,4,6-triiodo-3-(2-hydroxypropionamido)-5-(2,3-dihydroxypropylaminocarbonyl)phenyl]urea a. N,N'-bis[2,4,6-triiodo-3-(2-acetoxypropionamido)-5-(2,3-acetoxypropylaminocarbonyl)phenyl]urea.

N,N'-bis[3-amino-2,4,6-triiodo-5-(2,3-acetoxypropylaminocarbonyl)phenyl]urea (1.0 g, 0.71 mmol) prepared as described above and 2-acetoxypropionic acid chloride (4.0 ml) were mixed and stirred at 60° C. for 2 h and 14 h at 85° C. The solvents were evaporated and the residue was triturated with water (50 ml). The greenish solid was filtered off and used without purification in the next step. Yield: 0.92 g (79%).

$^1$H NMR (DMSO-$d_6$): 10.08–10.25 (m, 2H), 8.70–9.30 (m, 2H), 8.08–8.75 (m, 2H), 5.15–5.27 (m, 2H), 5.03–5.16 (m, 2H), 4.23–4.36 (m, 2H), 4.11–4.25 (m, 2H), 3.23–3.54 (m, 4H), 2.10 (s, 3H), 2.06 (2s, 15H), 1.47–1.55 (m, 6H). $^{13}$C NMR (DMSO-$d_6$): 170.7, 170.4, 170.0, 151.8, 150.1, 149.0, 144.5, 143.3, 143.2, 108.3, 107.9, 106.4, 97.7, 97.6, 70.5, 70.0, 69.9, 63.6, 63.5, 63.4, 21.5, 21.3, 21.0, 18.0.

b. N,N'-bis[2,4,6-triiodo-3-(2-hydroxypropionamido)-5-(2,3-dihydroxypropylaminocarbonyl)phenyl]urea.

N,N'-bis[2,4,6-triiodo-3-(2-acetoxypropionamido)-5-(2,3-acetoxypropylaminocarbonyl)phenyl]urea (0.85 g, 0.52 mmol) was dissolved in a mixture of methanol (10 ml) and 2M aqueous NaOH (2.5 ml) and the solution was stirred at room temperature for 2 h. The pH was then adjusted to 4 using a strongly acidic ion exchange resin, and, after filtration, evaporated to dryness. The residue was purified by preparative HPLC. Yield: 370 mg (51%).

$^1$H NMR (DMSO-$d_6$): 9.58–9.84 (m, 2H), 8.22–8.64 (m, 4H), 5.50–5.70 (m, 2H), 4.67 (br s, OH, 2H), 4.48 (br s, OH, 2H), 4.13–4.17 (m, 2H), 3.64–3.75 (m, 2H), 3.40–3.61 (m, 2H), 3.26–3.35 (m, 2H), 3.07–3.25 (m, 4H), 1.35–1.42 (m, 6H). $^{13}$C NMR (DMSO-$d_6$): 173.0, 172.8, 170.3, 170.2, 151.8, 10.2, 144.2, 143.9, 108.0, 99.5, 99.2, 97.8, 97.6, 97.5, 70.4, 70.3, 68.0, 64.4, 43.1, 21.5, 21.0. MS (ESP, m/e): 1374 ($M^+$, 20%), 1397 ([M+Na]$^+$, 100%).

EXAMPLE 13

N,N'-bis[2,4,6-triiodo-3-(2,3-dihydroxypropionoylamido)-5-(2,3-dihydroxypropylaminocarbonyl)phenyl]urea a. N,N'-bis[2,4,6-triiodo-3-(2,2-dimethyl-1,3-dioxalane-4-carboxamido)-5-(2,3-diacetoxypropylaminocarbonyl)phenyl]urea.

2,2-dimethyl-1,3-dioxalane-4 carboxylic acid potassium salt (1.50 g, 8.1 mmol) was suspended in dry ether (35 ml) and cooled to 0° C. Oxalyl chloride (1.03 g, 8.1 mmol) was added and the solution was stirred for 2 h at 0° C. and then for 24 h at ambient temperature. The mixture was filtered and the filtrate was evaporated. A solution of N,N'-bis[3-amino-2,4,6-triiodo-5-(2,3-acetoxypropylaminocarbonyl)phenyl]urea (1.9 g, 1.36 mmol) prepared as described above in dimethylacetamide (10 ml) was then added and the resulting solution was stirred for 60 h at ambient temperature. Addition of ether (60 ml) resulted in the formation of a precipitate which was further triturated with ether (50 ml) to give 1.88 g (84%) of the product.

$^1$H NMR (DMSO-$d_6$): 9.57–10.10 (m, 2H), 8.26–8.55 (m, 4H), 3.08–4.37 (m, 16H), 1.87–2.04 (m, 12H). $^{13}$C NMR (DMSO-$d_6$): 172.4, 170.9, 170.1, 150.1, 147.0, 144.4, 143.8, 141.9, 127.9, 100.1, 99.8, 99.6, 99.1, 97.7, 97.6, 97.4, 74.2, 70.4, 66.9, 66.8, 64.8, 64.4, 64.1, 43.1, 43.0, 37.9, 35.0, 21.8, 21.5. MS (ESP, m/e): 1656 ($M^+$, 100%), 1679 ([M+Na]$^+$, 80%).

b. N,N'-bis[2,4,6-triiodo-3-(2,3-dihydroxypropionoylamido)-5-(2,3-dihydroxypropylaminocarbonyl)phenyl]urea.

N,N'-bis[2,4,6-triiodo-3-(2,2-dimethyl-1,3-dioxalane-4-carboxamido)-5-(2,3-diacetoxypropylaminocarbonyl)phenyl]urea (0.60 g, 0.36 mmol) was mixed with $K_2CO_3$ (0.40 g, 2.8 mmol) in methanol (40 ml). The solution was stirred for 88 h, the solution was filtered and the filtrate evaporated to dryness. The residue was dissolved in water (20 ml) and the pH was adjusted to 2 using aqueous 2M HCl. After stirring for 3 h, the solution was evaporated to dryness and the residue was purified by preparative HPLC. Two isomeric fractions were separated and collected. Yield: 240 mg (fraction 1)+45 mg (fraction 2); 56%.
Physical data, fraction 1:
$^1$H NMR (DMSO-d$_6$): 9.67–9.90 (m, 2H), 8.23–8.60 (m, 4H), 3.06–3.84 (m, 16H), 4.02–4.20 (m, 8H). $^{13}$C NMR (DMSO-d$_6$): 171.0, 170.8, 170.3, 170.2, 151.8, 151.7, 150.2, 144.3, 144.1, 143.9, 143.8, 108.1, 108.0, 107.8, 99.5, 99.3, 99.2, 97.8, 97.6, 74.2, 70.4, 64.7, 64.4, 43.2, 43.1. MS (ESP, m/e): 1408 (M$^+$, 100%), 1431 ([M+Na]$^+$, 10%). Fraction 2: 9.62–10.05 (m, 2H), 8.25–8.60 (m, 4H), 5.65–5.90 (m, 2H), 4.62–4.90 (m, 4H), 4.42–4.53 (m, 2H), 4.02–4.10 (m, 2H), 3.40–3.82 (m, 10H), 3.05–3.32 (m, 4H).

EXAMPLE 14

N,N'-bis[2,4,6-triiodo-3-amino-5-(1,3-diacetoxyprop-2-ylaminocarbonyl)phenyl]urea a. N,N'-bis[3-nitro-5-(1,3-dihydroxyprop-2-ylaminocarbonyl)phenyl]urea.

The reaction was performed analogous to the synthesis described above for Example 10c starting from N,N'-bis(3-nitro-5-methoxycarbonylphenyl)urea (12.0 g, 28.7 mmol) and serinol (6.83 g, 75 mmol). The crude reaction product was purified by trituration with acetonitrile (2×50 ml), with water (200 ml) and with acetonitrile (3×50 ml) to give 95% pure product. Yield: 12.0 g (78%).

$^1$H NMR (DMSO-d$_6$): 10.06, 9.72 (2s, ArNH, 2H), 8.68–8.73 (m, 2H), 8.44–8.51 (m, 2H), 8.38–8.43 (m, 2H), 8.23–8.27 (m, 2H), 4.66–4.73 (m, 4H), 3.92–4.13 (m, 2H), 3.44–3.60 (m, 8H). $^{13}$C NMR (DMSO-d$_6$): 164.9, 164.6, 152.9, 148.6, 148.4, 141.9, 141.1, 137.0, 131.8, 124.9, 124.4, 117.1, 115.7, 115.3, 60.7, 54.8, 53.3.

b. N,N'-bis[2,4,6-triiodo-3-amino-5-(1,3-hydroxyprop-2-ylaminocarbonyl)phenyl]urea.

N,N'-bis[3-nitro-s-(1,3-dihydroxyprop-2-ylaminocarbonyl)phenyl]urea (5.6 g, 10.4 mmol) was dissolved in a mixture of methanol (100 ml) and water (14 ml) containing 2 M aqueous HCl (10.4 ml) and a Pd/C catalyst (10%, 0.5 g). Hydrogenation was carried out at 60 psi. The catalyst was filtered off, the methanol was evaporated and the aqueous solution was lyophilized. The residue was dissolved in a mixture of methanol (36 ml) and water (775 ml) and then, KICl$_2$ (32.9 g, 97 mmol) was added. After stirring for 72 h, a 2M aqueous solution of NaHSO$_3$ was added and the solid was filtered off. After washing the precipitate with methanol (3×50 ml), the residue was dried. Yield: 13.9 g (76%).

$^1$H NMR (DMSO-d$_6$): 7.90–8.36 (m, 4H), 5.32–5.40 (m, 4H) 3.30–4.25 (m, 14H). $^{13}$C NMR (DMSO-d$_6$): 170.1, 151.9, 149.1, 148.9, 148.8, 146.6, 143.1, 143.0, 88.8, 88.6, 83.0, 82.8, 81.5, 78.7, 78.6, 78.5, 76.9, 59.8, 53.6, 53.5. MS (ESP, m/e): 1254 ([M+Na]$^+$, 100%).

c. N,N'-bis[2,4,6-triiodo-3-amino-5-(1,3-diacetoxyprop-2-ylaminocarbonyl)phenyl]urea.

N,N'-bis[2,4,6-triiodo-3-amino-5-(1,3-hydroxyprop-2ylaminocarbonyl)phenyl]urea (4.0 g, 3.26 mmol) was suspended in a mixture of acetic anhydride (10 ml) and pyridine (10.5 ml) and the mixture was stirred for 16 h at ambient temperature. The solvents were evaporated and the residue was suspended in water (150 ml). The solid was filtered off, washed with aqueous 0.1 M HCl (2×50 ml), water (2×50 ml) and dried. Yield: 3.8 g (84%).

$^1$H NMR (DMSO-d$_6$): 8.55–8.95 (m, 2H), 8.10–8.35 (m, 2H), 5.36–5.68 (m, 4H), 4.10–4.20 (m, 8H), 3.83–3.95 (m, 2H), 1.99–2.07 (m, 12H). $^{13}$C NMR (DMSO-d$_6$): 170.7, 170.2, 149.0, 148.9, 148.7, 143.3, 143.2, 143.1, 89.2, 82.8, 78.5, 78.3, 78.2, 62.6, 47.4, 21.3. MS (ESP, m/e): 1422 ([M+Na]$^+$, 70%), 1478 ([M+C$_5$H$_5$N]$^+$, 100%).

EXAMPLE 15

N-[3-hydroxymethyl-5-(2,3-dihydroxypropylaminocarbonyl)-2,4,6-triiodophenyl]-N'[3,5-bis(2,3-dihydroxypropylaminocarbonyl)-2,4,6-triiodo)phenyl]urea a. 1-Hydroxymethyl-3-nitro-5-benzoic acid methyl ester.

1-Nitroisophthalic acid monomethyl ester (22.5 g, 100 mmol) was dissolved in dry THF (675 ml) and BF$_3$.Et$_2$O (25.2 ml, 200 mmol) was added. NaBH$_4$ (5.1 g, 135 mmol) was then added portionwise during 1 h. After stirring for 2 additional h, ethanol (20 ml) was added slowly followed by water (200 ml) and diethyl ether (400 ml). The phases were separated and the aqueous phase was extracted once with diethyl ether (100 ml). The combined organic phases were washed with a saturated aqueous solution of NaHCO$_3$, dried (Na$_2$SO$_4$) and evaporated. Yield: 20 g (96%). HPLC analysis indicated >95% purity of the product.

$^1$H NMR (CDCl$_3$): 8.72 (s, 1H), 8.42 (s, 1H), 8.32 (s, 1H), 4.86 (s, 2H), 3.97 (s, 3H), 2.37 (br s, 1H).

b. 1-Hydroxymethyl-3-nitro-5-(2,3-dihydroxypropylaminocarbonyl)benzene.

The methyl ester from Example 3a (20.5 g, 97 mmol) was mixed with 2,3-dihydroxypropylamine (9.6 g, 106 mmol) and the mixture was heated to 90° C. After 45 min, the pressure was reduced to 200 mm Hg and heating was continued for 2 h. The crude product, which was >95% pure according to HPLC analysis, was used without further purification in the next step. Yield: 22.8 g (87%).

$^1$H NMR (CD$_3$OD): 8.57 (s, 1H), 8.38 (s, 1H), 8.19 (s, 1H), 4.77 (s, 2H), 3.81–3.88 (m, 1H), 3.39–3.63 (m, 4H).

c. 3-Hydroxymethyl-5-(2,3-dihydroxypropylaminocarbonyl)aniline.

1-Hydroxymethyl-3-nitro-5-(2,3-dihydroxypropylaminocarbonyl)benzene (12.0 g, 44.4 mmol) was hydrogenated in methanol (150 ml) at 60 psi H$_2$ using Pd/C (10%, 100 mg) as the catalyst. The catalyst was removed by filtration and the residue was evaporated. Addition of methanol (10 ml) precipitated the product as a white solid which was filtered off and dried. Yield: 6.6 g (62%).

$^1$H NMR (CD$_3$OD): 7.05–7.09 (m, 1H), 6.98–7.03 (m, 1H), 6.83–6.87 (m, 1H), 4.53 (s, 2H), 3.77–3.85 (m, 1H), 3.8–3.59 (m, 4H), 3.32–3.42 (m, 1H) MS (ESP, m/e): 241 ([M+1]$^+$, 100%).

d. 3-Hydroxymethyl-5-(2,3-dihydroxypropylaminocarbonyl)-2,4,6-triiodoaniline.

3-Hydroxymethyl-5-(2,3-dihydroxypropylaminocarbonyl)aniline (500 mg, 2.1 mmol) was dissolved in water (175 ml) and an aqueous solution of KICl$_2$ (70%, w/w) was added in portions of 0.1 ml during 8 h. A total amount of 1.0 ml KICl$_2$ solution was added. After a total reaction time of 6 h, the solution was extracted with ethyl acetate (1000 ml) which was separated and washed with an aqueous solution of Na$_2$S$_2$O$_3$ (0.2M, 100 ml). Evaporation followed by purification by preparative HPLC gave 432 mg (33%) of the pure product.

$^1$H NMR (CD$_3$OD): 5.10 (s, 2H), 3.90–3.98 (m, 1H), 3.72 (ddd, J$_1$=0.7 Hz, J$_2$=4.2 Hz, J$_3$=11.4 Hz), 1H), 3.60 (dd, J$_1$=6.0 Hz, J$_2$=11.4 Hz, 1H), 3.49 (ddd, J$_1$=1.2 Hz, J$_2$=6.0 Hz, J$_3$=13.5 Hz, 1H), 3.37 (ddd, J$_1$=1.2 Hz, J$_2$=6.1 Hz, J$_3$=13.2 Hz, 1H), 2.62 (s, 1H), 2.28 and 2.34 (2s, 2H). MS (ESP, m/e): 618 (M$^+$, 100%), 640 ([M+Na]$^+$, 55%).

e. 3-Acetoxymethyl-5-(2,3-diacetoxypropylaminocarbonyl)-2,4,6-triiodoaniline.

3-Hydroxymethyl-5-(2,3-dihydroxypropylaminocarbonyl)-2,4,6-triiodoaniline (1.32 g, 2.1 mmol) was dissolved in pyridine (10 ml) containing acetic anhydride (10 ml). The mixture was stirred at room temperature for 2 h and CH$_2$Cl$_2$ (100 ml) and the solution was washed with water (3×25 ml). The organic phase was washed with water (3×50 ml) and a saturated aqueous solution of NaHCO$_3$ (2×50 ml). After drying (Na$_2$SO$_4$) and evaporation, the residue was purified by flash chromatography on a silica column using a mixture of CH$_2$Cl$_2$ and methanol (95:5) as the eluent. Yield: 1.30 g (82%).

$^1$H NMR (CDCl$_3$): 5.99 (br s, 1H), 5.52 (s, 2H), 5.25 (br s, 1H), 5.11 (s, 2H), 4.23–4.45 (m, 2H), 3.56–3.87 (m, 3H), 2.08 (s, 9H).

f. N-[3-acetoxymethyl-5-(2,3-diacetoxypropylaminocarbonyl)-2,4,6-triiodophenyl]-N'-[3,5-bis(2,3-diacetoxypropylaminocarbonyl)-2,4,6-triiodophenyl]urea.

3,5-Bis(2,3-diacetoxypropylaminocarbonyl)-2,4,6-triiodoaniline (260 mg, 0.30 mmol) was dissolved in dioxane (1.0 ml) and a solution of phosgene in toluene (1.93M, 1.8 ml) was added. The flask was tightly sealed and then heated to 60° C. for 17 h. After cooling to ambient temperature, the solvent was distilled off at reduced pressure. Dioxane (3 ml) was added and distilled off again. This procedure was repeated twice. Dioxane (1 ml) was added followed by 3-acetoxymethyl-5-(2,3-diacetoxypropylaminocarbonyl)-2,4,6-triiodoaniline (0.245 g, 0.31 mmol) and Hg(OCOCF$_3$)$_2$ (20 mg). The mixture was stirred for 16 h at ambient temperature, the solvent was evaporated and the residue was purified by preparative HPLC. Yield: 0.192 g (39%). MS (ESP, m/e): 1643 (M$^+$, 100%), 1665 ([M+Na]$^+$, 34%).

g. N-[3-hydroxymethyl-5-(2,3-dihydroxypropylaminocarbonyl)-2,4,6-triiodophenyl]-N'[3,5-bis(2,3-dihydroxypropylaminocarbonyl)-2,4,6-triiodophenyl]urea.

The product from Example 15f was dissolved in a mixture of methanol (5 ml) and water (5 ml) and the pH was adjusted to 12 using a 2 M aqueous solution of NaOH. After stirring for 2 h, the pH was adjusted to 6.5 using aqueous HCl and the solvents were evaporated. The product was purified using preparative HPLC. Yield: 68 mg (44%). MS (ESP, m/e): 1349 (M$^+$, 15%), 1372 ([M+Na]$^+$, 100%).

EXAMPLE 16

2,4,6-Triiodo-3-acetylamino-5-(1,3-dihydroxyprop-2-ylaminocarbonyl) phenylaminocarbonyl-2',4',6'-triiodo-3'-acetylamino-5'-(1,3-dihydroxyprop-2-ylaminocarbonyl)]benzene a. 1-Nitro-3-amino-5-benzoic acid methyl ester hydrochloride.

1-Nitro-3-aminobenzoic acid (15.0 g, 82.4 mmol) was dissolved in methanol (100 ml) and HCl gas was bubbled into the solution for 30 min. After stirring for 17 h at ambient temperature, the solvent was evaporated and the residue was washed with ether (3×50 ml) to give the product as a white solid. Yield: 15.8 g (82%).

$^1$H NMR (DMSO-d$_6$): 7.78–7.81 (m, 1H), 7.68–7.71 (m, 1H), 7.65–7.67 (m, 1H), 5.00 (s, NH$_3$, 3H) 3.83 (s, OCH$_3$, 3H).

b. 3-Nitro-5-methoxycarbonylphenylaminocarbonyl-(3'-nitro-5'-methoxycarbonylbenzene).

1-Nitro-3-amino-5-benzoic acid methyl ester hydrochloride (0.92 g, 4.72 mmol) and 5-nitroisophthalic acid monomethyl ester (1.06 g, 4.27 mmol) were suspended in a mixture of POCl$_3$ (4 ml) and toluene (15 ml). The mixture was heated until the solution was homogeneous and then, the solution was stirred for 16 h at ambient temperature. The solvents were evaporated and the oily residue was dissolved in CH$_2$Cl$_2$. The solution was washed with aqueous 0.1 M HCl (3×50 ml) and a saturated aqueous solution of NaHCO$_3$ (50 ml), treated with charcoal, dried (MgSO$_4$) and evaporated. The product was essentially pure by HPLC analysis. Yield: 1.25 g (66%).

$^1$H NMR (DMSO-d$_6$): 11.28 (s, 1H), 9.09 (t, J=1.8 Hz, 1H), 9.03 (t, J=1.8 Hz, 1H), 8.95 (t, J=1.7 Hz, 1H), 8.81 (t, J=1.6 Hz, 1H), 8.78 (t, J=1.7 Hz, 1H), 8.38 (2t, J$_1$=1.6 Hz, J$_2$=1.5 Hz, 1H), 3.96 (s, OCH$_3$, 3H), 3.93 (s, OCH$_3$, 3H). MS (ESP, m/e): 426 ([M+Na]$^+$, 100%), 442 ([M+K]$^+$, 14%).

C. 3-Nitro-5-(1,3-dihydroxyprop-2-ylaminocarbonyl)phenylaminocarbonyl-[3'-nitro-5'-(1,3-dihydroxyprop-2-ylaminocarbonyl)benzene].

3-Nitro-5-methoxycarbonylphenylaminocarbonyl-(3'-nitro-5'-methoxycarbonylbenzene) (0.40 g, 1.0 mmol) and serinol (0.23 g, 2.5 mmol) were mixed and heated to 95° C. After 30 min, the pressure was reduced to 200 mm Hg and heating was continued for 3 h. The reaction mixture was purified by preparative HPLC. Yield: 0.27 g (52%).

$^1$H NMR (DMSO-d$_6$): 11.2 (br s, 1H), 8.94–8.98 (m, 2H), 8.89–8.92 (m, 2H), 8.61–8.65 (m, 1H), 8.61 (d, J=7.2 Hz, 1H), 8.52–8.55 (m, 1H), 8.46 (d, J=7.8 Hz, 1H), 4.60–4.81 (m, 4H), 3.96–4.08 (m, 2H), 3.51–3.59 (m, 8H). MS (ESP, m/e): 522 (M$^+$, 100%), 504 ([M-H$_2$O]$^+$, 65%).

d. 3-Amino-5-(1,3-dihydroxyprop-2-ylaminocarbonyl)phenylaminocarbonyl-[3'-amino-5'-(1,3-dihydroxyprop-2-ylaminocarbonyl)benzene] dihydrochloride.

3-Nitro-5-(1,3-dihydroxyprop-2-ylaminocarbonyl)phenylaminocarbonyl-[3'-nitro-5'-(1,3-dihydroxyprop-2-ylaminocarbonyl)benzene] (1.03 g, 1.98 mmol) was hydrogenated in a solution containing methanol (40 ml), concentrated HCl (2 ml), water (2 ml) and a Pd/C catalyst (10%, 0.2 g) at 60 psi. The catalyst was filtered off and the solvent was evaporated. Water (150 ml) was then added and the solution was lyophilized. Yield: 0.98 g (93%).

$^1$H NMR (DMSO-d$_6$ containing 1% TFA): 10.83 (s, 1H), 8.25 (d, J=8.0 Hz, 1H), 8.23 (t, J=2.0 Hz, 1H), 8.12 (d, J=8.0 Hz, 1H), 8.07 (t, J=2.0 Hz, 1H), 8.03 (t, J=2.0 Hz, 1H), 7.73 (t, J=2.0 Hz, 1H), 7.70 (t, J=2 Hz, 1H), 7.46 (t, J=2.0 Hz, 1H), 4.30 (br s, 6H), 3.95–4.01 (m, 2H), 3.54 (t, J=5.5 Hz, 8H). MS (ESP, m/e): 461 (M$^+$, 100%).

e. 3-Amino-2,4,6-triiodo-5-(1,3-dihydroxyprop-2-ylaminocarbonyl)phenylaminocarbonyl-[3'-amino-2'-4'-6'-triiodo-5'-(1,3-dihydroxyprop-2-ylaminocarbonyl)benzene].

3-Amino-5-(1,3-dihydroxyprop-2-ylaminocarbonyl)phenylaminocarbonyl-[3'-amino-5'-(1,3-dihydroxyprop-2-ylaminocarbonyl)benzene] dihydrochloride (0.50 g, 0.94 mmol) was dissolved in a mixture of methanol (225 ml) and water (675 ml) and pH was adjusted to 2.0 with aqueous HCl. KICl$_2$ (1.91 g, 5.64 mmol) was added and the solution was stirred at 40° C. One more portion of KICl$_2$ (0.1 g) was added after 24 h and after 48 h, the reaction was terminated by the addition of an aqueous solution of NaHSO$_3$. After evaporation of the solvents, the residue was purified by preparative HPLC. Yield: 0.05 g (8.3%).

$^1$H NMR (DMSO-d$_6$): 9.85–10.05 (m, 1H), 8.87–9.00 (m, 1H), 7.80–8.15 (m, 1H), 5.52 (s, NH$_2$, 2H), 5.47 (s, NH$_2$, 2H), 4.40 (t, J=7.0 Hz, 2H), 4.15–4.24 (m, 2H), 4.06 (d, J=7.0 Hz, 1H), 4.04 (d, J=7.0 Hz, 1H), 3.78–3.85 (m, 3H), 3.57–3.64 (m, 3H), 3.40–3.56 (m, 2H). $^{13}$C NMR (DMSO-d$_6$): 170.3, 170.2, 165.7, 150.0, 149.9, 149.6, 148.9, 148.1, 148.0, 147.5, 141.7, 64.2, 59.7, 53.4. MS (ESP, m/e): 1215 (M$^+$, 100%).

f. 3-Acetylamino-2,4,6-triiodo-5-(1,3-dihydroxyprop-2-ylaminocarbonyl)phenylaminocarbonyl-[3'-acetylamino-2',4',6'-triiodo-5'-(1,3-dihydroxyprop-2-ylaminocarbonyl)benzene].

3-Amino-2,4,6-triiodo-5-(1,3-dihydroxyprop-2-ylaminocarbonyl)phenylaminocarbonyl-[3'-amino-2'-4'-6'-triiodo-5'-(1,3-dihydroxyprop-2-ylaminocarbonyl)benzene] (75 mg, 0.062 mmol) was dissolved in acetic anhydride (0.6 ml) containing concentrated sulfuric acid (0.04 ml). The mixture was heated to 60° C. for 75 min and, after cooling, the solvent was evaporated. The dark residue was dissolved in a mixture of methanol (0.35 ml) and water (0.15 ml), pH was adjusted to 10–11 using aqueous 2M NaOH and the solution was stirred at 50° C. for 5 h. After cooling to ambient temperature, pH was adjusted to 7 with aqueous 2M HCl and the solvent was evaporated. The residue was purified by preparative HPLC. Yield: 0.076 g (94%).

$^1$H NMR (DMSO-$d_6$): 10.27–10.48 (m, 1H), 9.97 (br s, 1H), 9.94 (br s, 1H), 8.21 (d, J=7.0 Hz, 1H), 8.11 (d, J=7.0 Hz, 1H), 4.43–4.56 (m, 4H), 3.72–3.88 (m, 2H), 3.60–3.70 (m, 4H), 3.40–3.60 (m, 4H), 2.07–2.08 (m, 6H). $^{13}$C NMR (DMSO-$d_6$): 169.9, 169.7, 168.2, 165.2, 151.0, 148.4, 144.7, 144.6, 144.3, 144.2, 142.8, 142.7, 59.6, 59.5, 53.6, 31.1. MS (ESP, m/e): 1300 (M$^+$, 100%).

EXAMPLE 17

2,4,6-Triiodo-3-hydroxyacetylamino-5-(1,3-dihydroxyprop-2-ylaminocarbonyl)phenylaminocarbonyl-2',4',6'-triiodo-3'-hydroxyacetylamino-5-(1,3-dihydroxyprop-2-ylaminocarbonyl)]benzene a. 2,4,6-Triiodo-3-amino-5-(1,3-diacetoxyprop-2-ylaminocarbonyl)phenylaminocarbonyl-2',4',6'-triiodo-3-amino-5'-(1,3-diacetoxyprop-2-ylaminocarbonyl)]benzene.

3-Amino-2,4,6-triiodo-5-(1,3-dihydroxyprop-2-ylaminocarbonyl)phenylaminocarbonyl-[3'-amino-2'-4'-6'-triiodo-5'-(1,3-dihydroxyprop-2-ylaminocarbonyl)benzene] (0.10 g, 0.082 mmol) prepared as described in Example 15 above, was dissolved in a mixture of acetic anhydride (5 ml) and pyridine (5.5 ml). The mixture was stirred at 40–45° C. for 16 h, the solvents were evaporated and the residue was dissolved in ethyl acetate (25 ml). After washing with water (25 ml), aqueous 0.5 M HCl, water and saturated aqueous solution of NaHCO$_3$, the solution was dried (MgSO$_4$) and the solvent was evaporated. Yield: 0.11 g (100%).

$^1$H NMR (DMSO-$d_6$): 9.94–10.04 (m, 1H); 8.67 (d, J=7.0 Hz, 1H), 8.65 (d, J=7.0 Hz, 1H), 5.54 (s, NH$_2$, 2H), 5.50 (s, NH$_2$, 2H), 4.27–4.40 (m, 2H), 4.11–4.16 (m, 8H), 2.01–2.03 (m, 12H). $^{13}$C NMR (DMSO-$d_6$): 170.7, 170.4, 170.3, 165.7, 149.6, 149.5, 149.0, 148.2, 147.6, 141.8, 139.8, 62.6, 47.4, 21.3. MS (ESP, m/e): 1385 (M$^+$, 100%).

b. 2,4,6-Triiodo-3-hydroxyacetylamino-5-(1,3-dihydroxyprop-2-ylaminocarbonyl)phenylaminocarbonyl-2',4',6'-triiodo-3'-hydroxyacetylamino-5'-(1,3-dihydroxyprop-2-ylaminocarbonyl)]benzene. 2,4,6-Triiodo-3-amino-5-(1,3-diacetoxyprop-2-ylaminocarbonyl)phenylaminocarbonyl-2',4',6'-triiodo-3'-amino-5'-(1,3-diacetoxyprop-2-ylaminocarbonyl)]benzene (94 mg, 0.068 mmol) was suspended in acetoxyacetyl chloride (3 ml) and the mixture was stirred at 65° C. for 4 h, allowed to cool and then evaporated. The residue was dissolved in a mixture of methanol (3 ml), water (3 ml) and aqueous 1M NaOH (0.50 ml) and the solution was stirred for 3 h. The solution was neutralized using a strongly acidic cation exchange resin and the solvents were evaporated. The residue was purified by preparative HPLC. Yield 90 mg (100%). MS (ESP, m/e): 1582 (M$^+$, 100%).

EXAMPLE 18

2,4,6-Triiodo-3-acetylamino-5-(2,3-dihydroxypropylaminocarbonyl)phenylaminocarbonyl-2',4',6'-triiodo-3'-acetylamino-5'-(2,3-dihydroxypropylaminocarbonyl)]benzene a. 3-Nitro-5-(2,3-dihydroxypropylaminocarbonyl)phenylaminocarbonyl-[3'-nitro-5'-(2,3-dihydroxypropylaminocarbonyl)benzene].

3-Nitro-5-methoxycarbonylphenylaminocarbonyl-(3'-nitro-5'-methoxycarbonylbenzene) (1.21 g, 3.0 mmol) was suspended in aminopropan-2,3-diol (0.55 g, 6.0 mmol) and the mixture was heated to 90° C. After 30 min, the pressure was reduced to 200 mm Hg and heating was continued for 90 min. The product was purified by preparative HPLC. Yield: 0.73 g (47%).

$^1$H NMR (DMSO-$d_6$): 11.32 (s, 1H), 9.02 (t, J=6.0 Hz, 1H), 8.93–8.97 (m, 3H), 8.88 (t, J=1.7 Hz, 1H), 8.86 (t, J=6.0 Hz, 1H), 8.68 (t, J=1.5 Hz, 1H), 8.51 (t, J=1.8 Hz, 1H), 3.62–3.72 (m, 2H), 3.36–3.48 (m, 2H), 3.33–3.36 (m, 4H), 3.18–3.29 (m, 2H), 3.09 (s, 4H). MS (ESP, m/e): 545 ([M+Na]$^+$, 65%), 522 (M$^+$, 100%), 504 ([M-18]$^+$, 19%).

b. 3-Amino-2,4,6-triiodo-5-(2,3-dihydroxypropylaminocarbonyl)phenylaminocarbonyl-[3'-amino-2'-4'-6'-triiodo-5'-(2,3-dihydroxypropylaminocarbonyl)benzene].

3-Nitro-5-(2,3-dihydroxypropylaminocarbonyl)phenylaminocarbonyl-[3'-nitro-5'-(2,3-dihydroxypropyl-aminocarbonyl)benzene] (2.0 g, 2.0 mmol) was hydrogenated in a solution containing methanol (70 ml), concentrated HCl (4 ml), water (4 ml) and a Pd/C catalyst (10%, 0.6 g) at 60 psi. The catalyst was filtered off and the solvent was evaporated. Water (150 ml) was then added and the solution was lyophilized. Yield: 2.0 g (98%). The crude product was used immediately without purification in the next step: The product was dissolved in a mixture of methanol and water (1:3, 1200 ml) and an aqueous solution of KICl$_2$ (5.34 g, 22.6 mmol) was added. The reaction mixture was stirred at 40° C. for 30 h and then an 0.5M aqueous solution of NaHSO$_3$ (1 ml) was added. After evaporation of the solvents, the residue was purified by preparative HPLC. Yield: 0.63 g (13%).

$^1$H NMR (DMSO-$d_6$): 9.86–10.00 (m, 1H), 8.18–8.45 (m, 2H), 5.44–5.47 (m, 4H), 4.66–4.78 (m, 2H), 4.45–4.55 (m, 2H), 3.59–3.78 (m, 2H), 3.41–3.56 (m, 2H), 3.30–3.43 (m, 2H), 3.10–3.36 (m, 2H). $^{13}$C NMR (DMSO-$d_6$): 170.7, 165.6, 149.9, 148.5, 147.8, 147.1, 140.8, 108.0, 85.2, 84.4, 80.9, 79.2, 78.3, 70.0, 64.0, 42.6. MS (ESP, m/e): 1216 (M$^+$, 100%), 1238 ([M+Na]$^+$, 20%.

c. 2,4,6-Triiodo-3-acetylamino-5-(2,3-dihydroxypropylaminocarbonyl)phenylaminocarbonyl-2',4',6'-triiodo-3'-acetylamino-5'-(2,3-dihydroxypropylaminocarbonyl)]benzene.

3-Amino-2,4,6-triiodo-5-( 2,3-dihydroxypropylaminocarbonyl) phenylaminocarbonyl-[3'-amino-2'-4'-6'-triiodo-5'-(2,3-dihydroxypropylaminocarbonyl)benzene] (100 mg, 0.082 mmol) was dissolved in acetic anhydride (7 ml), one drop of concentrated sulfuric acid was added and the mixture was stirred at 60° C. for 1.5 h. The solvent was evaporated and the residue was dissolved in a mixture of methanol and water (3:1, 10 ml) and pH was adjusted to 13 with a 2M aqueous solution of NaOH. The mixture was stirred for 16 h at 50° C., diluted with water (20 ml) and pH was adjusted to neutral using an strongly acidic ion exchange resin. The solvents were removed by evaporation and the residue was purified by preparative HPLC. Yield: 75 mg (71%). MS (ESP, m/e): 1301 (M$^+$, 81%), 1324 ([M+Na]$^+$, 100%.

EXAMPLE 19

2,4,6-Triiodo-3-hydroxyacetylamino-5-(2,3-dihydroxypropylaminocarbonyl)phenylaminocarbonyl-2',4',6'-triiodo-3'-hydroxyacetylamino-5'-(2,3-dihydroxypropylaminocarbonyl)]benzene a. 2,4,6-Triiodo-3-amino-5-(2,3-diacetoxypropylaminocarbonyl)phenylaminocarbonyl-2',4',6'-triiodo-3'-amino-5'-(2,3-diacetoxypropylaminocarbonyl)]benzene.

3-Amino-2,4,6-triiodo-5-(2,3-dihydroxypropylaminocarbonyl)phenylaminocarbonyl-[3'-amino-2'-4'-6'-triiodo-5'-(2,3-dihydroxypropylaminocarbonyl)benzene] (100 mg, 0.082 mmol), prepared according to Example 17, was dissolved in a mixture of acetic anhydride (2 ml) and pyridine (2 ml). The mixture was stirred at ambient temperature for 17 h, the solvents were evaporated and the residue was dissolved in ethyl acetate (50 ml). After washing with an aqueous solution of HCl (0.1M, 25 ml), a saturated aqueous solution of $NaHCO_3$, drying ($Na_2SO_4$) and evaporation, the residue was purified by preparative HPLC. Yield: 100 mg (88%).

$^1$H NMR (DMSO-$d_6$): 9.89–10.27 (m, 1H), 8.56–8.70 (m, 2H), 5.54 (s, 2H), 5.51 (s, 2H), 5.06–5.13 (m, 2H), 4.25–4.36 (m, 2H), 4.16–4.22 (m, 2H), 3.30–3.58 (m, 4H), 2.02 (s, 12H).

MS (ESP, m/e): 1385 (M$^+$, 100%), 1464 ([M+pyridine]$^+$, 19%).

b. 2,4,6-Triiodo-3-hydroxyacetylamino-5-(2,3-dihydroxypropylaminocarbonyl)phenylaminocarbonyl-2',4',6'-triiodo-3'-hydroxyacetylamino-5'-(2,3-dihydroxypropylaminocarbonyl)]benzene.

2,4,6-Triiodo-3-amino-5-(2,3-diacetoxypropylaminocarbonyl)phenylaminocarbonyl-2',4',6'-triiodo-3'-amino-5'-(2,3-diacetoxypropylaminocarbonyl)]benzene (35 mg, 0.025 mmol) was dissolved in acetoxyacetyl chloride (1 ml) and the mixture was heated to 70° C. for 1.5 h. After cooling to ambient temperature, the solvent was evaporated and the residue was dissolved in a mixture of methanol and water (3:1, 1 ml). A 1M aqueous solution of NaOH (0.23 ml) was added, and, after stirring for 15 min, water (20 ml) was added and the solution was neutralized with a strongly acidic ion exchange resin. The solvents were evaporated and the residue was purified by preparative HPLC. Yield: 14 mg (61%).

MS (ESP, m/e): 1332 (M$^+$, 100%).

EXAMPLE 20

2,4,6-Triiodo-3-(2-hydroxypropionylamino)-5-(2,3-dihydroxypropylaminocarbonyl)phenylaminocarbonyl-2',4',6'-triiodo-3'-(2-hydroxypropionylamino)-5'-(2,3-dihydroxypropylaminocarbonyl]benzene 2,4,6-Triiodo-3-amino-5-(2,3-diacetoxypropylaminocarbonyl)phenylaminocarbonyl- 2',4',6'-triiodo-3'-amino-5'-(2,3-diacetoxypropylaminocarbonyl)]benzene (100 mg, 0.072 mmol) was dissolved in α-acetoxypropionyl chloride (1 ml) and the mixture was stirred at 40° C. for 17 h. The solvent was evaporated and the residue was suspended in a mixture of methanol and water (1:1, 4 ml). An aqueous solution of NaOH (1M, 0.5 ml) was added and the solution was stirred for 5 h. Water (20 ml) was added and pH was adjusted to neutral using a strongly acidic cation exchange resin. The solvent was evaporated and the residue was purified by preparative HPLC. Yield: 33 mg (43%).

$^1$H NMR (DMSO-$d_6$): 10.16–10.55 (m, 1H), 9.54–9.86 (m, 2H), 8.40–8.65 (m, 2H), 5.60 (br s, 2H), 4.70 (br s, 2H), 4.46 (br s, 2H), 4.08–4.22 (m, 2H), 3.60–3.71 (m, 2H), 3.32–3.58 (m, 2H), 3.15–3.32 (m, 2H), 3.04–3.22 (m, 4H), 1.39 (d, J=7.0 Hz, 6H). $^{13}$C NMR (DMSO-$d_6$): 172.4, 170.0, 169.8, 169.7, 150.7, 148.0, 143.8, 143.2, 143.1, 142.3, 104.6, 100.8, 100.2, 100.0, 99.8, 97.2, 96.9, 95.0, 90.7, 90.5, 69.8, 67.6, 64.0, 42.7, 21.0. MS (ESP, m/e): 1361 (M$^+$, 100%), 1383 ([M+Na]$^+$, 25%).

EXAMPLE 21

Di[2,4,6-triiodo-N,N'-(2,3-dihydroxypropyl)-3,5-acetylaminophenyl]ether a. 3,5-Dinitroanisole.

Sodium (575 mg, 25 mmol) was dissolved in absolute methanol (100 ml). 1,3,5-Trinitrobenzene (4.26 g, 20 mmol) was then added and the solution was stirred overnight. After evaporation of the solvent, water was added and the precipitate was filtered off, washed with water and dried. The material was used without purification in the next step. Yield: 3.4 g (86%).

$^1$H NMR (CDCl$_3$): 8.65 (t, J=2.0 Hz, 1H), 8.06 (d, J=2.0 Hz, 2H), 4.01 (s, 1H).

b. 3,5-Dinitrophenol.

3,5-Dinitroanisole (1.36 g, 6.9 mmol) and concentrated aqueous HBr (50 ml) was heated to reflux temperature for 16 h. After cooling to ambient temperature, the solid precipitate was filtered off, washed with water and dried. Yield: 325 mg (26%).

$^1$H NMR (CDCl$_3$): 8.64 (t, J=2.0 Hz, 1H), 8.04 (d, J=2.0 Hz, 2H), 2.0 (br s, 1H).

c. 3,5-Diacetylaminophenol.

3,5-Dinitrophenol (325 mg, 1.77 mmol) was dissolved in glacial acetic acid (20 ml) and hydrogenated at 60 psi using a Pd-C catalyst (10%, 50 mg). The reaction mixture was filtered and acetic anhydride (2 ml) was added. The solution was heated to 100° C. and then allowed to cool again. The solvents were removed by evaporation and the residue was purified by chromatography on silica gel using a mixture of methanol and ethyl acetate (10:90) as the eluent. Yield: 90 mg (24%).

$^1$H NMR (CD$_3$OD): 7.24 (t, J=2.0 Hz, 1H), 6.92 (d, J=2.0 Hz, 2H), 2.12 (s, 6H).

d. 3,5-Dinitrophenyl-3',5'-diacetylaminophenylether.

3,5-Diacetylaminophenol (90 mg, 0.43 mmol) and trinitrobenzene (0.111 g, 0.52 mmol) were dissolved in dry DMF (10 ml) and K$_2$CO$_3$ (0.124 g, 0.90 mmol) was added. After stirring for 17 h, water (20 ml) was added and the solution was extracted with ethyl acetate. After washing with water (2×10 ml), drying (Na$_2$SO$_4$) and evaporation of the solvent, the residue was purified by chromatography on silica gel using ethyl acetate as the eluent. Yield: 0.121 g (75%). MS (ESP, m/e): 375 ([M+1]$^+$, 100%), 397 ([M+Na]$^+$, 39%), 413 ([M+K]$^+$, 35%).

e. Di(3,5-diacetylaminophenyl)ether.

3,5-Dinitrophenyl-3',5'-diacetylaminophenylether (0.12 g, 0.32 mmol) was dissolved in glacial acetic acid (5 ml) and heated to the reflux temperature. Iron powder (0.3 g) was added in portions during 5 min. After refluxing for 2 h, the solution was allowed to cool to ambient temperature, acetic anhydride (1.5 ml) was added and heating was continued for another 2 h. The solvents were then removed by evaporation, the residue was treated with ethyl acetate, filtered and evaporated. The residue was dissolved in acetone and the solution was filtered though a pad of silica gel. Evaporation of the solvent gave 84 (66%) of the product.

$^1$H NMR (CD$_3$OD): 7.62 (s, 2H), 7.08 (s, 4H), 2.12 (s, 12H). MS (ESP, m/e): 399 ([M+1]$^+$, 62%), 421 ([M+Na]$^+$, 41%), 437 ([M+K]$^+$, 100%).

f. Di(3,5-diacetylamino-2,4,6-triiodophenyl)ether.

Iodination of di(3,5-diacetylaminophenyl)ether is carried out using the standard procedures for iodination of activated aromatics, e.g. using $KICl_2$ in an aqueous solution or in a mixture of water and an alcohol as described in the literature (see for example EP-A-501875 and DE-A-2629228). Purification of the product is performed by chromatography or recrystallization.

g. Di[2,4,6-triiodo-N,N'-(2,3-dihydroxypropyl)-3,5-acetylaminophenyl]ether.

Alkylation of di(3,5-diacetylamino-2,4,6-triiodophenyl) ether is carried out analogous to similar reactions described in the literature, e. g. using sodium methoxide as the base in a proper solvent such as propylene glycol, and 3-chloropropane-1,2-diol (see, for example: U.S. Pat. No. 4,250,113). The product is purified by preparative HPLC.

EXAMPLE 22

Di[3-hydroxyacetylamino-5-(2,3-dihydroxypropylaminocarbonyl)-2,4,6-triiodophenyl]methanol a. Di(3-acetylphenenyl)ketone.

Acetophenone (57.6 g, 0.48 mmol) and $AlCl_3$ (160 g, 1.2 mol) were mixed and heated to 100° C. under an argon atmosphere for 30 min. After cooling to ambient temperature, $CCl_4$ (300 ml) was added and the mixture was heated to reflux temperature for 4 h. After cooling to ambient temperature, a mixture of water and concentrated HCl (300 ml, 1:1) was added. The aqueous phase was extracted with $CHCl_3$ (3×200 ml) and the combined organic phases were evaporated. The residue was dissolved in 70% ethanol (400 ml) and the solution was briefly heated to reflux temperature. Evaporation of the solvents followed by recrystallization from aqueous acetone gave the pure product. Yield: 49.9 g (77%).

$^1$H NMR ($CDCl_3$): 8.36 (t, J=1.5 Hz, 2H), 8.20 (dt, $J_d$=7.8 Hz, $J_t$=1.5 Hz, 2H), 7.98 (dt, $J_d$=7.7 Hz, $J_t$=1.5 Hz, 2H), 7.62 (t, J=7.7 Hz, 2H), 2.65 (s, 6H). MS (ESP, m/e): 268 ($M^+$, 100%).

b. Di(3-nitro-5-carboxyphenyl)ketone.

Di(3-acetylphenenyl)ketone (60.0 g, 0.224 mol) was dissolved in concentrated sulfuric acid (400 ml) and the solution was cooled to 0° C. A mixture of concentrated sulfuric acid (120 ml) and concentrated nitric acid (120 ml) was then added dropwise and the solution was then stirred at ambient temperature for 17 h. After stirring for another 24 h at 40° C. and for 6 h at 60° C., the reaction mixture was poured onto ice and the precipitate was collected, washed with water and dried. Yield: 77.6 g (96%).

$^1$H NMR (DMSO-$d_6$): 8.83 (t, J=1.8 Hz, 2H), 8.67 (t, J=1.8 Hz, 2H), 8.57 (t, J=1.8 Hz, 2H), 3.9 (br s, 2H). MS (ESP$^-$, m/e): 359 ([M-1]$^-$, 100%).

c. Di(3-nitro-5-carboxyphenyl)ketone dimethyl ester dimethyl ketal.

Di(3-nitro-5-carboxyphenyl)ketone (10.0 g, 28 mmol) was dissolved in methanol (250 ml) containing concentrated sulfuric acid (20 ml) and the solution was heated to reflux temperature for 17 h. The solvent was evaporated, water (70 ml) and ethyl acetate (300 ml) were added and the organic phase was separated and dried. After evaporation of the solvent, the residue was dissolved in THF containing $K_2CO_3$ (3.87 g, 28 mmol) and $CH_3I$ (5.0 ml) and the solution was stirred at ambient temperature for 70 h. The reaction mixture was filtered and evaporated to dryness and the residue was purified by preparative HPLC. Yield: 2.6 g (25%).

$^1$H NMR ($CDCl_3$): 8.76–8.78 (m, 2H), 8.58 (t, J=1.7 Hz, 2H), 8.41 (t, J=1.6 Hz, 2H), 3.98 (s, 6H), 3.19 (s, 6H). MS (EI, m/e): 403 ([M-$OCH_3$]$^+$, 100%).

d. Di[3-nitro-5-(2,3-dihydroxypropylaminocarbonyl) phenyl]ketone.

Di(3-nitro-5-carboxyphenyl)ketone dimethyl ester dimethyl ketal (1.0 g, 2.3 mmol) was dissolved in methanol (3.0 ml) containing aminopropane-2,3-diol (0.84 g, 9.2 mmol) and the mixture was heated to 95° C. for 2.5 h at 200 mm Hg. After cooling to ambient temperature, the solvent was removed by evaporation and the residue was purified by preparative HPLC. Yield: 0.78 g (67%).

$^1$H NMR (DMSO-$d_6$): 9.03–9.15 (m, 2H), 8.90–9.03 (m, 2H), 8.58–8.73 (m, 4H), 4.38 (br s, 2H), 4.12 (br s, 2H), 3.61–3.70 (m, 2H), 3.39–3.48 (m, 2H), 3.35 (br s, 2H), 3.33 (br s, 2H), 3.15–3.26 (m, 2H). $^{13}$C NMR (DMSO-$d_6$): 163.9, 148.3, 138.1, 137.9, 136.9, 134.4, 126.9, 126.4, 70.5, 64.3, 43.8. MS (ESP$^-$, m/e): 504 (M$^-$, 100%).

e. Di[3-amino-5-(2,3-dihydroxypropylaminocarbonyl) phenyl]methanol.

Di[3-nitro-5-(2,3-dihydroxypropylaminocarbonyl) phenyl]ketone (0.70 g, 1.4 mmol) was dissolved in methanol (40 ml) and was hydrogenated at 60 psi using a Pd/C catalyst (10%, 0.20 g). The catalyst was filtered off and the solvent was evaporated. Analysis by $^1$H NMR indicated complete conversion to the product. Yield: 0.62 g (100%).

$^1$H NMR (DMSO-$d_6$): 8.36–8.57 (m, 1H), 7.77–8.35 (m, 3H), 7.04–7.72 (m, 4H), 5.62–5.75 (m, 1H), 5.10 (br s, 1H), 4.23 (br s, 1H), 4.06 (br s, 2H), 3.60–3.85 (m, 4H), 2.91–3.40 (m, 10H). MS (ESP, m/e): 449 ($M^+$, 100%).

f. Di[3-amino-5-(2,3-dihydroxypropylaminocarbonyl)-2,4, 6-triiodophenyl]methanol.

Iodination of di[3-amino-5-(2,3-dihydroxypropylaminocarbonyl)phenyl]methanol is carried out using the standard procedures for iodination of activated aromatics, e. g. using $KICl_2$ in an aqueous solution or in a mixture of water and an alcohol as described in the literature (see for example EP-A-501875 and DE-A-2629228). Purification of the product is performed by chromatography or recrystallization.

g. Di[3-hydroxyacetylamino-5-(2,3-dihydroxypropylaminocarbonyl-2,4,6-triiodophenyl] methanol.

Acylation of di[3-amino-5-(2,3-dihydroxypropylaminocarbonyl)-2,4,6-triiodophenyl] methanol using acetoxyacetyl chloride is carried out analogous to Example 19b. The crude product is then hydrolyzed with aqueous NaOH. The product is purified by preparative HPLC.

We claim:

1. A compound of formula (I)

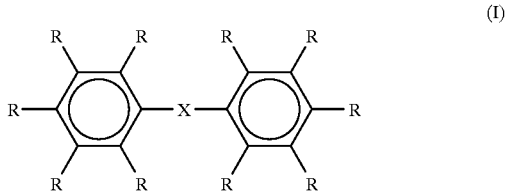

wherein each $C_6R_5$ moiety may be the same or different; each R denotes a hydrogen or iodine atom or a group M, two or three non-adjacent R groups on each $C_6R_5$ moiety denoting iodine atoms and one, two or three R groups on each $C_6R_5$ moiety denoting M groups, each $C_6R_5$ moiety being a triiodophenyl group or a group in which each R is other than hydrogen; X denotes a group $CONR^1$ where $R^1$ is hydrogen or a $C_{1-6}$-alkyl or alkoxy group optionally substituted by hydroxy, alkoxy, oxa or oxo linking the two $C_6R_5$ groups;

and each M is independently a non-ionic hydrophilic moiety and isomers thereof.

2. A compound as claimed in claim 1 wherein each M is a monohydroxy- or polyhydroxy-alkyl group.

3. A compound as claimed in claim 1 wherein the two $C_6R_5$ groups are non-identically substituted.

4. A compound as claimed in claim 1 wherein at least one $C_6R_5$ group is of formula

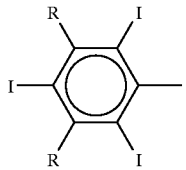

wherein the two R groups are the same or different.

5. A compound as claimed in claim 1 wherein at least one $C_6R_5$ group is of formula

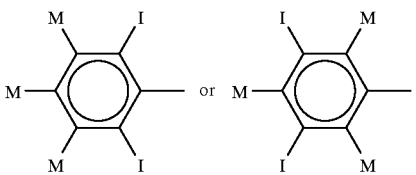

wherein the M groups are the same or different.

6. A compound as claimed in claim 1 wherein the M groups are straight-chain or branched $C_{1-10}$-alkyl groups which have one or more $CH_2$ or CH moieties replaced by oxygen or nitrogen atoms and which are substituted by one or more groups selected from oxo, hydroxy, amino, carboxyl derivative, and oxo substituted sulphur and phosphorus atoms.

7. A compound as claimed in claim 1 wherein the M groups are polyhydroxyalkyl, hydroxyalkoxyalkyl or hydroxypolyalkoxyalkyl groups optionally attached to the phenyl group via an amide linkage.

8. A compound as claimed in claim 1 wherein the M groups are selected from

—CONH—$CH_2CH_2OH$,

—CONH—$CH_2CHOHCH_2OH$,

—CONH—$CH(CH_2OH)_2$,

—CON$(CH_2CH_2OH)_2$,

—$CONH_2$,

—$CONHCH_3$,

—$OCOCH_3$,

—N$(COCH_3)$H,

—N$(COCH_3)C_{1-3}$-alkyl,

—N$(COCH_3)$-mono, bis or tris-hydroxy $C_{1-4}$-alkyl,

—N$(COCH_2OH)$-mono, bis or tris-hydroxy $C_{1-4}$-alkyl,

—C$(COCH_3)$ (mono, bis or tris-hydroxy $C_{1-4}$-alkyl)$_2$,

—N—$(COCH_2OH)_2$,

—CON$(CH_2CHOHCH_2OH)$ $(CH_2CH_2OH)$,

—CONH—$C(CH_2OH)_3$ and

—CONH—$CH(CH_2OH)$ $(CHOHCH_2OH)$.

9. A compound as claimed in claim 1 wherein the M groups are polyhydroxy-$C_{1-4}$-alkyl groups.

10. A diagnostic composition comprising a compound of formula I as defined in claim 1 together with at least one physiologically tolerable carrier or excipient.

11. A compound as claimed in claim 1 which is 2,4,6-Triiodo-3-(2-hydroxypropionylamino-5-(2,3-dihydroxypropylaminocarbonyl)phenylamino-carbonyl-2',4',6'-triiodo-3'-(2-hydroxypropionylamno)-5'(2,3-dihydroxypropyl-aminocarbonyl)-benzene.

* * * * *